US007906665B2

(12) United States Patent
Lin et al.

(10) Patent No.: US 7,906,665 B2
(45) Date of Patent: Mar. 15, 2011

(54) SOLID CATALYST SYSTEM FOR BIODIESEL PRODUCTION

(75) Inventors: Victor Shang-Yi Lin, Ames, IA (US); Yang Cai, Ames, IA (US); Carla Kern, Ames, IA (US); Joel I. Dulebohn, Lansing, MI (US); Jennifer A. Nieweg, Ames, IA (US)

(73) Assignees: Iowa State University Research Foundation, Inc., Ames, IA (US); Claytec, Inc., East Lansing, MI (US)

( * ) Notice: Subject to any disclaimer, the term of this patent is extended or adjusted under 35 U.S.C. 154(b) by 371 days.

(21) Appl. No.: 12/121,918

(22) Filed: May 16, 2008

(65) Prior Publication Data

US 2009/0112007 A1    Apr. 30, 2009

Related U.S. Application Data

(60) Provisional application No. 60/983,875, filed on Oct. 30, 2007.

(51) Int. Cl.
*C11C 3/00* (2006.01)
(52) U.S. Cl. ......................................... 554/167; 502/172
(58) Field of Classification Search .................. 554/167; 502/172
See application file for complete search history.

(56) References Cited

U.S. PATENT DOCUMENTS

| | | | |
|---|---|---|---|
| 3,751,275 A * | 8/1973 | Oken | 106/640 |
| 5,134,242 A | 7/1992 | Le et al. | |
| 6,040,473 A | 3/2000 | Knebel et al. | |
| 6,204,424 B1 | 3/2001 | Yadav et al. | |
| 6,946,109 B2 | 9/2005 | Pinnavaia et al. | |
| 7,790,651 B2 | 9/2010 | Lin et al. | |
| 2008/0021232 A1 | 1/2008 | Lin et al. | |

FOREIGN PATENT DOCUMENTS

| | | |
|---|---|---|
| DE | 19602035 A1 | 7/1997 |
| EP | 0535747 A1 | 4/1993 |
| EP | 0535757 A1 | 4/1993 |
| EP | 1380637 A1 | 1/2004 |
| GB | 2 269 377 A * | 2/1994 |
| GB | 2269377 A | 2/1994 |
| WO | WO-2008/013551 A1 | 1/2008 |
| WO | WO-2009058324 A1 | 5/2009 |

OTHER PUBLICATIONS

Svikle, D. et al: "Intensification of the esterification process of rosin" Latvijas Psr Zinatnu Akademijas Vestis, Kimijas Serija , (No. 2), 261-2, 1961.*

(Continued)

*Primary Examiner* — Deborah D Carr
(74) *Attorney, Agent, or Firm* — Schwegman, Lundberg & Woessner, P.A.

(57) ABSTRACT

The invention provides efficient, inexpensive, and environmental friendly catalysts and catalyst systems. The catalysts can be used to catalyze esterification and/or transesterification reactions, for example, for the preparation of biodiesel. Kiln dust, such as cement kiln dust (CKD) or lime kiln dust (LKD) can be used to convert a variety of feedstock acids and/or esters to biodiesel in high yield under mild conditions. The CKD and LKD catalyst systems are recyclable esterification or transesterification catalysts that can be used to prepare biodiesel, such as methyl soyate, from various feedstocks, including vegetable oils and animal fats.

26 Claims, 9 Drawing Sheets

OTHER PUBLICATIONS

Consolati et al: "A positron annihilation study on the hydration of cement pastes" Jan. 26, 2007, Materials Chemistry and Physics, Elsevier, pp. 264-268.*

Harbottle et al: "Degradation of 2-chlorobenzoic acid in stabilized/solidified .soil systems" Aug. 22, 2007, International Biodeterioration and Biodegradation, pp. 173-181 , p. 175, see col. 2, paragraph 3.*

Ekolu S et al: "Pessimism effect of externally applied chlorides on expansion due to delayed ettringite formation: Proposed mechanism" Cement and Concrete Research, vol. 36, No. 4, Apr. 1, 2006, pp. 688-696, see figure 8.*

"International Application Serial No. PCT/US2008/012309, International Search Report mailed Feb. 18, 2009", 4 pgs.

"International Application Serial No. PCT/US2008/012309, Written Opinion mailed Feb. 18, 2009", 8 pgs.

"International Application Serial No. PCT/US06/32482, International Search Report mailed May 23, 2007", 3 pgs.

"International Application Serial No. PCT/IUS06/32482", Written Opinion mailed May 23, 2007, 4 pgs.

Bender, M., "Economic Feasibility Review for Community-Scale Farmer Cooperatives for Biodiesel", *Bioresource Technology*, 70, (1999), 81-87.

Brunet, F., et al., "Application of $^{29}$Si Homonuclear and $^{1}H^{29}$Si Heteronuclear NMR Correlation to Structural Studies of Calcium Silicate Hydrates", *J. Phys. Chem. B.*, 108, (2004), 15494-15502.

Chen, J. J., et al., "Solubility and Structure of Calcium Silicate Hydrate", *Cement and Concrete Research*, 34, (2004), 1499-1519.

Clark, J. H., "Solid Acids for Green Chemistry", *Acc. Chem. Res.*, 35, (2002), 791-797.

Consolati, G., et al., "A positron annihilation study on the hydration of cement pastes", *Materials Chemistry and Physics*. 101, (2007), 264-268.

Diasakou, M., et al., "Kinetics of the Non-Catalytic Transesterification of Soybean Oil", *Fuel*, 77(12), 1998 , 1297-1302.

Ekolu, S. O, et al., "Pessimum effect of externally applied chlorides on expansion due to delayed ettringite formation: Proposed mechanism", *Cement and Concrete Research*, 36, (2006), 688-696.

Gryglewicz, S., "Alkaline-Earth Metal Compounds as Alcoholysis Catalysts for Ester Oils Synthesis", *Applied Catalysis A: General*, 192, (2000), 23-28.

Gryglewicz, S., "Rapeseed Oil Methyl Esters Preparation Using Heterogeneous Catalysts", *Bioresource Technology*, 70, (1999), 249-253.

Harbottle, M. J., et al., "Degradation of 2-chlorobenzoic acid in stabilised/solidified soil systems", *International Biodeterioration & Biodegradations*, (2007), 173-181.

Kiss, A. A., et al., "Solid Acid Catalysts for Biodiesel Production—Towards Sustainable Energy", *Adv. Synth. Catal.*, 348, (2006), 75-81.

Ma, F., et al., "Biodiesel Production: A Review", *Bioresource Technology*, 70, (1999), 1-15.

Ogoshi, T., et al., "Soap and Related Products: Palm and Lauric Oil", *JAOCS*, 62(2), (1985), 331-335.

Sohn, J. R., et al., "Acidic Properties of CaO-SiO$_2$ Binary Oxide Catalyst and Activity for Acid Catalysis", *Korean J. of Chem. Eng.*, 14(3), (1997), 192-197.

Suppes, G. J., et al., "Calcium Carbonate Catalyzed Alcoholysis of Fats and Oils", *JAOCS*, (78)2, 2001 , 139-145.

Svikle, D., et al., "Intensification of the estrification process of rosin", *Chemical Abstracts Service*, (1961), 261-261.

Ngamcharussrivichai, C. , et al., "Modified Dolomites as Catalysts for Palm Kernal Oil Transesterification", *Journal of Molecular Catalysis*, 276, (2007),24-33.

"U.S. Appl. No. 11/506,417, Non Final Office Action mailed Sep. 24, 2009", 10 pgs.

"U.S. Appl. No. 11/506,417, Non-Final Office Action mailed Sep. 24, 2009", 10 pgs.

"U.S. Appl. No. 11/506,417, Notice of Allowance mailed May 3, 2010", 4 pages.

"U.S. Appl. No. 11/506,417, Response filed Jan. 25, 2010 to Non Final Office Action mailed Sep. 24, 2009", 9 pgs.

"U.S. Appl. No. 11/506,417, Response filed Mar. 2, 2009 to Restriction Requirement mailed Jan. 28, 2009", 6 pgs.

"U.S. Appl. No. 11/506,417, Response filed Jul. 24, 2009 to Restriction Requirement mailed Jun. 25, 2009", 7 pgs.

"U.S. Appl. No. 11/506,417, Restriction Requirement mailed Jan. 28, 2009", 6 pgs.

"U.S. Appl. No. 11/506,417, Restriction Requirement mailed Jun. 25, 2009", 7 pgs.

"International Application Serial No. PCT/US2008/012309, International Preliminary Report on Patentability mailed Jan. 13, 2010", 11 pgs.

* cited by examiner

Recyclability Test

SOLID CATALYST SYSTEM FOR BIODIESEL PRODUCTION

RELATED APPLICATIONS

This application claims priority under 35 U.S.C. §119(e) to U.S. Provisional Patent Application No. 60/983,875, filed Oct. 30, 2007, which is incorporated herein by reference.

BACKGROUND OF THE INVENTION

Biodiesel is becoming increasingly useful as a biodegradable, nontoxic diesel fuel (Ma and Hanna, *Bioresource Technology* 1999, 70, 1-15). Examples of biodiesel include soy diesel (methyl soyate), rapeseed methyl ester, and various vegetable and animal fat methyl esters. Biodiesel fatty acid methyl esters (FAME) have been recently accepted as a viable alternative to traditional petroleum-derived solvents that are of environmental concern and are under legislative pressure to be replaced by biodegradable substitutes that result in reduced environmental impact. Although interest in biodiesel is rapidly increasing, the process by which it is synthesized has not substantially changed in recent years.

Soy diesel is currently prepared commercially by an energy and labor intensive process wherein soybean oil is reacted with methanol at elevated temperature (often 140-150° F.), and often under elevated pressure, in the presence of sodium methoxide as a homogeneous catalyst. This process is called "transesterification". Isolation of the desired methyl soyate from the highly caustic (toxic) catalyst and other products, such as glycerol, involves a precise neutralization process with strong acids, such as hydrochloric acid (HCl), and extensive washes with water to remove the resulting sodium chloride (NaCl) salt. Also, glycerol must be separated from the sodium chloride salt by vacuum distillation. Because glycerol has a significantly high boiling point, the distillation becomes a costly and energy intensive operation (see Bender, M., *Bioresource Technology* 1999, 70, 81; Diasakou et al., *Fuel* 1998, 77, 1297; Ogoshi and Miyawaki, *J. Am. Oil Chem. Soc.* 1985, 62, 331; Suppes et al., *J. Am. Oil Chem. Soc.* 2001, 78, 139).

Current biodiesel preparation processes do not allow the catalyst to be recycled, due to the high solubility of sodium methoxide in methanol. Additionally, the labor and materials required for the neutralization, separation, and removal of the catalyst creates economic and environmental concerns. To circumvent these issues, researchers worldwide have been developing solid catalysts for the transesterification of oils to biodiesel. For example, various basic metal oxides, such as magnesium methoxide, calcium oxide, calcium alkoxide, and barium hydroxide, have been demonstrated to be active catalysts for transesterification (Gryglewicz, S., *Applied Catalysis, A: General* 2000, 192 (1), 23-28). However, these solid base catalysts have little or no recyclability due at least in part to the solubility of the solid metal oxides and hydroxides in methanol (Gryglewicz, S., *Bioresource Technology* 1999, 70 (3), 249-253).

Accordingly, there is a need for efficient, inexpensive, and environmentally friendly catalysts for biodiesel production that do not have the solubility, separation, and recyclability problems associated with currently known catalysts. There is also a need for new methods for efficient, inexpensive, and environmentally friendly biodiesel production that do not have the problems that are associated with the currently known methods.

SUMMARY

The invention provides a kiln dust composition and methods of using kiln dust as a catalyst. Cement kiln dust (CKD) has been found to be an efficient, inexpensive, and environmental friendly catalyst for biodiesel production. Other calcium oxide containing dusts, such as lime kiln dust (LKD) and Portland cement, can be used in place of, or in combination with CKD, to provide the catalyst compositions of the invention.

It was found that the simple combination of cement kiln dust, methanol, and soybean oil did not effectively result in conversion of the soybean oil to methyl soyate. Even after heating this mixture for prolonged periods of time, the cement kiln dust did not sufficiently catalyze the desired transesterification reaction. However, it was surprisingly discovered that dispersing the kiln dust in an alcoholic solvent, such as methanol, and heating the mixture for a period of time sufficient to activate the kiln dust provided a robust and recyclable transesterification catalyst system. A variety of calcium oxide containing particles can be activated by this procedure, the catalyst composition can catalyze esterification reactions and/or transesterification reactions, and the catalyst can be recycled several times.

Accordingly, the invention provides a recyclable esterification or transesterification catalyst system that includes kiln dust or Portland cement, and a $(C_1-C_5)$alkanol, wherein the surface area of the kiln dust or Portland cement is about 0.2 $m^2$ per gram to about 10 $m^2$ per gram, and wherein the kiln dust or Portland cement has been activated by contact with the $(C_1-C_5)$alkanol. The activation of the catalyst can be carried out at a suitable activation temperature, such as above about 20° C., above about 25° C., or above about 30° C. Depending on the alkanol used, the activation temperature can be at about the reflux temperature of that alkanol. In some embodiments, the temperature can be about 65° C., about 78° C., about 82° C., about 97° C., or about 100° C.

The surface area of the kiln dust can vary depending on the type selected for the production process. In various embodiments, the surface area can also be about 0.2 $m^2$ per gram to about 15 $m^2$ per gram, about 0.3 $m^2$ per gram to about 10 $m^2$ per gram, about 0.5 $m^2$ per gram to about 5 $m^2$ per gram, about 1 $m^2$ per gram to about 4 $m^2$ per gram, or about 1 $m^2$ per gram to about 2 $m^2$ per gram. The kiln dust can include one or more of calcium oxide (CaO), calcite ($CaCO_3$), anhydrite ($CaSO_4$), sodium, potassium, magnesium, or quartz ($SiO_2$). In some embodiments, the kiln dust will contain more calcium oxide than any other single alkaline earth metal component.

The kiln dust can contain about 10 mass % to about 80 mass % calcium atoms, about 15 mass % to about 65 mass % calcium atoms, about 20 mass % to about 60 mass % calcium atoms, or about 10 mass % to about 50 mass % calcium atoms. The kiln dust can also contain about 30-40 mass % calcium, or about 35% calcium by mass. The kiln dust can contain at least about 15 wt. %, at least about 30 wt. %, at least about 45 wt. %, at least about 50 wt. %, or at least about 55 wt. % calcium oxide, for example, either before or after a calcination, e.g., in its preparation or upon composition analysis. The kiln dust can contain up to about 95 wt. % calcium oxide, for example, either before or after a calcination, e.g., in its preparation or upon composition analysis. The kiln dust can be a cement kiln dust, a lime kiln dust, or the catalyst can be Portland cement, or a combination thereof. Additionally, the kiln dust can be CKD-5, CKD-BP, or a combination thereof.

The catalyst system can include a solid acid, a molecular sieve, or both. The acid can be an acidic mesoporous aluminum silicate mixed oxide particles. The molecular sieve particles absorb or adsorb water. The solid acids and molecular sieve particles can be used at any step of methods, depending on the conditions of the starting material and the desired process conditions.

The ($C_1$-$C_5$)alkanol used in the catalyst system can be methanol or ethanol, or a straight chain or branched ($C_3$-$C_5$) alkanol. The catalyst system can include cement kiln dust, lime kiln dust, or a combination thereof. The catalyst system can further include a fatty acid or an ester, for example, one that is converted to a biodiesel.

The invention further provides a method for preparing a fatty acid ($C_1$-$C_5$)alkyl ester that includes contacting an oil with an effective amount of a kiln dust and a ($C_1$-$C_5$)alcohol to provide a reaction mixture, under conditions so that the kiln dust catalyzes formation of a corresponding fatty acid ($C_1$-$C_5$)alkyl ester. The oil can be a glyceride-containing vegetable oil, or a glyceride-containing animal oil, wherein glycerol is produced as a by-product of the transesterification. The oil can be a feedstock of used cooking oil, and/or the feedstock oil can further include free fatty acids, for example, from animal fats, such as poultry fat. The method can be carried out in a batch reactor, or in a fixed bed flow-through reactor, for example, a column reactor.

Various amounts of alkanol can be used in the method. Depending upon the desired speed and economics of the reaction, higher or lower molar ratios of the alkanol can be employed. The molar ratio of the ($C_1$-$C_5$)alcohol to the oil can be about 600:1 to about 3:1. For example, suitable ratios include ratios of about 560:1, about 100:1, about 93:1, about 50:1, about 40:1, about 37:1, about 20:1, about 10:1, about 5:1, or about 3:1.

The kiln dust can be recovered and reused in a subsequent method for preparing a fatty acid ($C_1$-$C_5$)alkyl ester. Various types of kiln dust can be recycled and reused several times, for example, 5, 10, 15, 17, or 20 or more times.

The fatty acid portion of the glyceride-containing vegetable or animal oil can include an optionally unsaturated $C_{10}$-$C_{24}$ alkyl chain, and wherein the $C_{10}$-$C_{24}$ alkyl chain optionally includes one or more (for example, 1, 2, 3, or 4) sites of unsaturation, epoxidation, hydroxylation, or a combination thereof.

The formation of the ester can be carried out without added solvent other than the ($C_1$-$C_5$)alcohol. The formation of the ($C_1$-$C_5$)alkyl ester can be carried out at an elevated temperature, for example, above about 40° C. Depending on the reaction conditions, the formation can be carried out 50° C. to about 130° C., for example, at about 65° C., about 78° C., about 82° C., about 97° C., or about 100° C. The formation of the ester can also be carried out at a pressure greater than 1 atmosphere. For example, the formation of the ester can be carried out at about 20 psi to about 150 psi, such as at about 90 psi or about 100 psi.

The reaction mixture that includes the kiln dust and the ($C_1$-$C_5$)alcohol can be prepared prior to contacting the cement kiln dust and the ($C_1$-$C_5$)alcohol with the oil and/or fatty acid. The kiln dust and the ($C_1$-$C_5$)alcohol can be heated prior to contacting with the oil and/or fatty acid.

The glyceride-containing animal oil can include free fatty acids and optionally water. In such cases, the method can include, in any order, drying the animal oil by contacting the animal oil with a molecular sieve; immobilizing the free fatty acids on a solid acid; and optionally separating the molecular sieve and the immobilized free fatty acids from the glyceride-containing animal oil prior to contacting the glyceride-containing animal oil to the kiln dust.

The invention also provides methods for preparing biodiesel from animal fats. Accordingly, the invention provides a method for preparing fatty acid ($C_1$-$C_5$)alkyl esters from a feedstock that comprises one or more fatty acids and optionally one or more fatty acid glycerol esters. The method can include combining the feedstock, a ($C_1$-$C_5$)alcohol, cement kiln dust, lime kiln dust, or Portland cement catalysts; optionally an acid, and optionally molecular sieve particles, under conditions wherein the catalyst catalyzes the formation of fatty acid ($C_1$-$C_5$)alkyl esters, and glycerol when a fatty acid glycerol ester is present.

The invention further provides a method for preparing fatty acid methyl esters from a feedstock that includes one or more fatty acids and optionally one or more fatty acid glycerol esters by preparing a mixture that includes kiln dust (or Portland cement), an alkanol, for example, methanol, and optionally molecular sieve particles; heating the suspension to above about 30° C., for example, about 40° C., about 50° C., about 60° C., about 67° C., or about 70-100° C.; contacting the kiln dust to the feedstock to provide a reaction mixture; heating the reaction mixture to provide the fatty acid alkyl esters; and separating the fatty acid alkyl esters from the reaction mixture. In various embodiments of the invention, the kiln dust can be cement kiln dust or lime kiln dust. As in other embodiments throughout this description, the kiln dust can be replaced with Portland cement.

The invention also provides a method for preparing fatty acid alkyl esters from a feedstock that includes poultry fat. The method can include contacting poultry fat that includes free fatty acids with a solid acid so as to immobilize free fatty acids on the solid acid; contacting the poultry fat with molecular sieve particles to provide dried poultry fat; optionally filtering the solid acid and immobilized free fatty acids from the poultry fat, and optionally filtering the molecular sieve particles from the dried poultry fat; contacting the poultry fat with kiln dust or Portland cement, and methanol to provide a reaction mixture; heating the reaction mixture to an elevated temperature, for example, above about 40° C., to provide the fatty acid alkyl esters; and separating the fatty acid alkyl esters from the reaction mixture.

In one embodiment, the alkanol can be methanol and the elevated temperature can be the reflux temperature of the alkanol. Any effective amount of kiln dust can be employed. The wt. % of kiln dust can be about 0.1 wt. % to about 50 wt. %, about 2 wt. % to about 30 wt. %, about 3 wt. % to about 25 wt. %, about 4 wt. % to about 15 wt. %, or about 3 wt. % to about 10 wt. %, with respect to the weight of a feedstock material, such as a glyceride-containing vegetable or animal oil, or a dried poultry fat. In certain embodiments, 3 wt. % to about 5 wt. %, or about 4 wt. % of kiln dust provides a suitable amount of catalyst. In some embodiments, about 0.5 wt. %, about 1 wt. %, about 3 wt. %, about 4 wt. %, about 5 wt. %, about 10 wt. %, or about 15 wt. % of kiln dust provides a suitable amount of catalyst. The reaction conditions can also include use of pressure greater than one atmosphere (e.g., about 50-150 psi), the use of sonication, cavitation, ultrasound, or a combination thereof.

In some embodiments, the biodiesel products can contain residual amounts of detectable calcium. The residual calcium can be detected by standard techniques well known to those of skill in the art, such as inductively coupled plasma (ICP) Optical Emission Spectroscopy or ICP-Mass Spectroscopy. The product can contain, for example, about 1 ppm to about 1000 ppm of calcium atoms, typically about 5 ppm to about 500 ppm, or about 50 ppm to about 500 ppm, depending on reaction conditions and the technique used to separate the products from the reaction mixture. The calcium can be, for example, calcium atoms, calcium ions, or calcium compounds, such as calcium oxide or calcium carbonate.

The invention further provides a method for producing methyl soyate that includes contacting soybean oil, methanol, and kiln dust, under conditions wherein the kiln dust catalyzes the formation of glycerol and the methyl soyate. The conditions can include elevated temperature and/or pressure of greater than one atmosphere. The conditions can also include the use of sonication, cavitation, ultrasound, or a combination thereof.

BRIEF DESCRIPTION OF THE DRAWINGS

The following drawings form part of the present specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

DETAILED DESCRIPTION

Definitions

Figure 1:
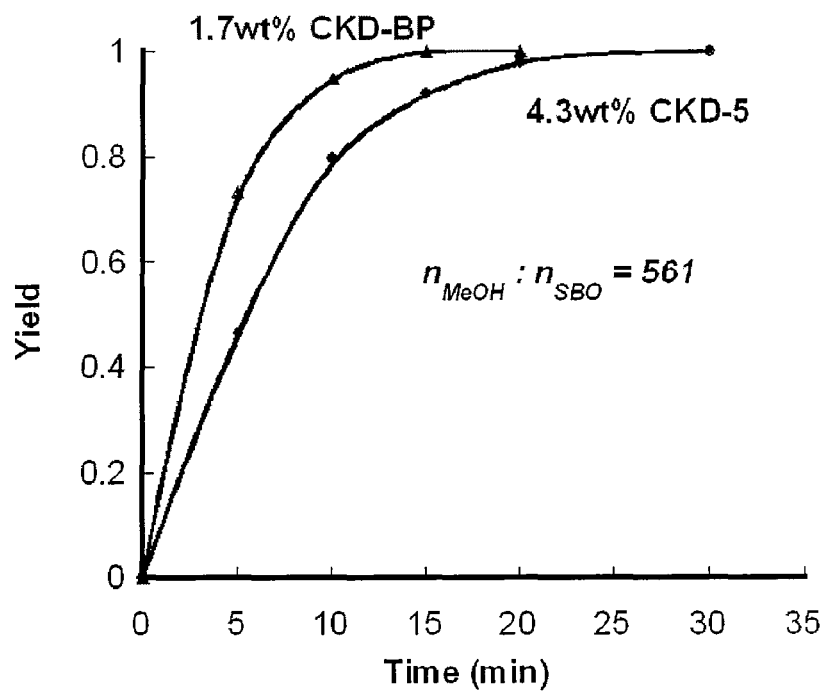
FIG. 1 illustrates catalytic conversion of soybean oil to biodiesel by CKD catalysts, according on one embodiment of the invention. CKD-5 (4.3 wt. % solid catalyst with respect to weight of oil) shows a complete conversion within 30 minutes. Using 1.7 wt. % CKD-BP, the reaction was complete in 15 minutes. Reaction conditions: 7.5 mL soybean oil in 180 mL MeOH; molar ratio of MeOH to oil was 561; volume ratio of MeOH to oil was 24.

Cement kiln dust ("CKD") is a by-product of the manufacture of cements, such as Portland Cement. CKD is a fine-grained solid and is a highly alkaline waste material that is removed from cement kiln exhaust gas. This material is comprised of fine particles gathered by dust collection systems during the cement manufacturing process. CKD particles typically have a particle size between about 0.1 and about 100 microns, and a specific gravity typically in the range of about 2.6 to about 2.8. They consist of particulate mixtures of partially calcined and untreated raw feed, clinker dust, and fuel ash, enriched with sulfates, halides and other volatiles. CKD is typically disposed in land-based disposal units, i.e., landfills, waste piles, or surface impoundments.

About 6 million metric tons of kiln dust is disposed each year by cement kilns. About 5.1 million tons are buried on-site and 900,000 tons are shipped off-site for use in stabilizing other wastes (such as sewage sludge) or as a soil additive on farms ("Report to Congress on Cement Kiln Dust," United States Environmental Protection Agency, Office of Solid Wastes, December 1993."). The potential for air pollution near the cement kilns has triggered research activities aimed at finding new applications for CKD during the last decade (see Daugherty and Wist, *Bull. Am. Ceram. Soc.*, 54 (1975) 189).

The terms "CKD-BP", "CKD-ESP", "CKD-5" and refer to types of CKD batches recovered from the production of Portland Cement. Based on elemental analysis and X-ray powder diffraction analysis, CKD-BP typically has about 38 wt. % calcium where more than about 80% of the calcium is in the form of calcium oxide. CKD-ESP typically has about 31 wt. % calcium with more than about 80% of the calcium in the form of calcium carbonate. CKD-5 typically has about 40 wt. % calcium where about 50% of the calcium is in the form of calcium oxide, and the remaining calcium is primarily in the form of calcium carbonate and/or calcium silicates.

The terms "by-pass CKD" and "CKD-BP" refers to kiln dust that is recovered from the alkali bypass of precalciner kilns, which have been observed to be typically coarser, more calcined, and concentrated with alkali volatiles than CKD that is not recovered from alkali bypass units, such as CKD batches designated as, for example, CKD-5 or CKD-ESP. CKD-BP is recovered from an alkali bypass system, which is employed to reduce the amount of the volatile components in a kiln pre-heater system.

An alkali bypass system removes kiln exhaust gases containing highly concentrated volatile components from the kiln system. Kiln exhaust gases, at about 1100° C., are extracted from a kiln through an extraction duct. The kiln exhaust gases are then passed into a cooling chamber and mixed therein with cooling air from a fan so as to reduce the temperature of the gases to about 400° C. to about 450° C. Volatile components in the kiln exhaust gases are then condensed on the surface of the dust by the decreasing gas temperature. The temperature of the gases is then lowered to about 150° C. by spraying a mist of water in a conditioning tower. The dust in the gases is then collected by an electrostatic precipitator and remaining gases are exhausted into the atmosphere through a fan. The dust collected by the conditioning tower and the electrostatic precipitator is disposed of as waste because the dust contains volatile components on the particle surfaces. The term "ESP" refers to electrostatic precipitation, which is one of the methods used to the capture kiln dust, and is a term used to refer to kiln dust recovered in this manner.

Lime kiln dust ("LKD") is a by-product of the manufacture of lime cement. LKD is mixtures of dust from finely ground limestone fed into kilns and fly ash from the fuel (e.g., coal, fuel oil, natural gas) used to heat the kilns. In the kilns, limestone ($CaCO_3$) is converted to quick lime (CaO). Lime kiln dust (LKD) is physically similar to cement kiln dust but chemically quite different. LKD can vary chemically depending on whether high-calcium lime (chemical lime, hydrated lime, quicklime) or dolomitic lime is being manufactured. The particle size of LKD can be about 50 nanometer to about 3 mm in diameter or length (depending on shape), typically about 100 nanometer to about 2 mm for the largest dimension. The surface area can be about 0.05 $m^2$/g to about 5 $m^2$/g, typically about 0.1 $m^2$/g to about 2 $m^2$/g. The particles can be spheroid or irregularly shaped.

In Cement and Concrete Terminology (ACI Committee 116), flyash is defined as "the finely divided residue resulting from the combustion of ground or powdered coal, which is transported from the firebox through the boiler by flue gases." Flyash is a by-product of coal-fired electric generating plants. Two classifications of flyash are produced, according to the type of coal used. Anthracite and bituminous coal produces flyash classified as Class F. Class C flyash is produced by burning lignite or subbituminous coal. Class C flyash is preferable for the applications presented in the Green Building Guide and is the main type offered for residential applications from ready-mix suppliers. An elemental analysis of flyash affords the following data for its composition:

| | Fly ash (% by weight) |
|---|---|
| $SiO_2$ | 46.8 |
| $Al_2O_3$ | 23.9 |
| $Fe_2O_3$ | 15.8 |
| CaO | 4.7 |
| $Na_2O$ | 0.8 |
| $K_2O$ | 1.6 |
| MgO | 0.9 |
| $SO_3$ | 1.2 |
| LOI | 2.4 |

The terms "to transesterify", "transesterifying", and "transesterification" refer to the alcoholysis of the glyceryl esters of a fat or oil with an alcohol, such as a ($C_1$-$C_4$)alkanol or ($C_1$-$C_5$)alkanol, to form newly formed esters and glycerol. The alkanol of the newly formed ester is derived from the alcohol used in the transesterification reaction. With respect to the transesterification of a mono-, di-, or triglyceride to provide a corresponding ($C_1$-$C_4$)alkyl ester and glycerol, the glycerol portion of the glyceride is replaced by a ($C_1$-$C_4$) alcohol, thus liberating glycerol from the mono-, di-, or triglyceride. In biodiesel production, glycerol can be separated from biodiesel by gravitational settling, centrifugation, distillation, or combinations thereof.

The terms "ester", "($C_1$-$C_4$)alkyl ester" and "fatty acid ($C_1$-$C_4$)alkyl ester" should be read in the context in which they are presented. One skilled in the art will readily recognize that the term "ester" will typically refer to the starting material ester, such as from a glyceride, vegetable oil, an animal oil, or other feedstock oil, and the corresponding "($C_1$-$C_4$)alkyl ester" refers to the product of a transesterification of the oil. Likewise, the term "fatty acid ($C_1$-$C_4$)alkyl ester" refers to a ($C_1$-$C_4$)alkyl ester of a starting material fatty acid or starting material fatty acid glyceryl ester.

Fatty acids can vary in carbon chain length and in the number of unsaturated bonds. Vegetable oils are typically made of a combination of fatty acids. Common vegetable oils include canola, coconut, corn, cottonseed, crambe, palm, peanut, rapeseed, soybean, and sunflower oils. These oils contain varying amounts of fatty acids, including combinations of $C_{10}$-$C_{30}$ fatty acids, or $C_{16}$-$C_{24}$ fatty acids, typically with 0, 1, 2, or 3 sites of unsaturation in each carbon chain. Some examples of these fatty acids include lauric, myristic, palmitic, stearic, oleic, linoleic, and linolenic acids. Animal fats and oils are typically made of combinations of fatty acids as well. Animal oils can be provided in various forms, including lard and tallow.

The term "feedstock" refers to a quantity of one or more fatty acid glycerol esters, one or more fatty acids, optionally other substances, and combinations thereof. Feedstocks include vegetable oils and animal oils, such as animal fats and restaurant waste oils. A feedstocks can refer to a large quantity of the acids and esters, for example, about one to one hundred kilograms.

The term "fatty acid ($C_1$-$C_4$)alkyl ester" refers to a fatty acid that has been esterified with a ($C_1$-$C_4$)alkanol. Throughout this description, a ($C_1$-$C_4$)alkanol can be replaced with a ($C_1$-$C_5$)alkanol, and vice versa, depending on the context of its use.

The term "glyceride-containing vegetable or animal oil" refers to a vegetable or animal oil that contains mono-, di-, or tri-esters of glycerol.

The term "$C_{10}$-$C_{24}$ fatty acid ester" refers to the ester of a $C_{10}$-$C_{24}$ fatty acid wherein the fatty acid portion of the molecule can be saturated or can have one or more sites of unsaturation, epoxidation, hydroxylation, or a combination thereof. For example, the fatty acid ester can have 1, 2, 3, 4, or more sites of unsaturation, epoxidation, hydroxylation, or a combination thereof. In certain embodiments, specific examples include methyl palmitate (a hexadecanoic acid methyl ester), methyl oleate (a (9Z)-octadec-9-enoic acid), methyl stearate (a octadecanoic acid methyl ester), methyl linoleate (a cis, cis-9,12-octadecadienoic acid methyl ester), methyl linolenate, various hydrogenated versions thereof, other alkyl esters thereof, and any combinations thereof. These esters can be prepared by condensation of the acids and an alkanol, such as methanol. The $C_{10}$-$C_{24}$ carbon chains can be branched or unbranched, and can be of various intermediate lengths, such as $C_{16}$-$C_{24}$, $C_{10}$-$C_{18}$, $C_{10}$-$C_{20}$, $C_{12}$-$C_{18}$, or $C_{12}$-$C_{20}$. Fatty acids of any chain length from about four carbons to about thirty carbons can be used in the context of this invention.

The terms "mono-, di-, or tri-ester of glycerol" refer to a glycerol molecule wherein one, two, or three hydroxyl groups of the glycerol have lost a hydrogen atom and have formed an ester linkage with an appropriate number of organic acids.

The term "methyl soyate" refers to methyl esters of the fatty acids or fatty acid moieties in soybean oil.

The term "acid portion of an ester" refers to the carboxyl (—C(=O)—O—) moiety of the ester.

The term "free alcohol of an/the ester" refers to the alkanol moiety of an ester after the alkanol portion has been hydrolyzed, alcoholyzed, or otherwise freed from the carboxyl moiety of the ester.

The terms "($C_1$-$C_5$)alcohol" and "($C_1$-$C_5$)alkanol" refer to a carbon or group of carbon atoms that contains a hydroxyl group. Examples include methanol, ethanol, propanol, iso-propanol, butanol, iso-butanol, sec-butanol, pentanol, sec-pentanol, and pivalylol. A ($C_1$-$C_5$)alkanol can be any one of these groups, or a combination thereof. A ($C_1$-$C_4$)alkanol is a similar category with a maximum of four carbon atoms in the molecule.

A "solid acid catalyst" is a material that contains acidic sites that can catalyze the esterification of free fatty acid. Examples include, but are not limited to, for example, Al-MCM, zeolites, sulfonic-functionalized SBA or MCM materials, and the like.

The term "acidic mesoporous aluminum silicate mixed oxide (Al-MCM)" refers to a particle, typically about 1 nm to about 100 nm in diameter, often about 1 nm to about 20 nm in diameter, that is a porous composite of aluminum oxides and silicon oxides, and which has acidic sites on the particle surface. Al-MCM can be used as a solid acid, for example, to sequester alkaline materials in a reaction mixture.

A "molecular sieve" is a material containing small pores of a precise and uniform size that is used as an adsorbent for gases and/or liquids. Molecular sieves often function as a desiccant. A typical molecular sieve, such as molecular sieve 4A, can adsorb water up to 22% of its own weight. Often they are made of aluminosilicate minerals, clays, porous glasses, microporous charcoals, zeolites, active carbons, or synthetic compounds that have open structures through which small molecules, such as nitrogen and water can diffuse. Molecular sieve 3A (pore size 3 Å) adsorbs NIH3 and $H_2O$, but not $C_2H_6$, and is suitable for drying polar liquids and a variety of nonpolar liquids. Molecular sieve 4A (pore size 4 Å) adsorbs $H_2O$, $CO_2$, $SO_2$, $H_2S$, $C_2H_4$, $C_2H_6$, $C_3H_6$, and EtOH. Molecular sieve 4A will not adsorb $C_3H_8$ and higher hydrocarbons, and is a suitable sieve for drying nonpolar liquids and gases.

Methods of Preparing/Activating the Catalyst System

The catalyst is an esterification or transesterification catalyst that includes kiln dust that has a surface area of, for example, about 0.05 $m^2$ per gram to about 10 $m^2$ per gram about 0.1 $m^2$ per gram to about 5 $m^2$ per gram about 0.3 $m^2$ per gram to about 3 $m^2$ per gram. The kiln dust can be cement kiln dust or lime kiln dust. A recyclable esterification or transesterification catalyst system can be prepared by combining the cement kiln dust and methanol. The reactivity of the kiln dust can be increased by contacting it with methanol at a temperature of above room temperature, for example, about 25-80° C., about 35-70° C., or about 50-65° C., or at temperature up to and/or including a reflux temperature of a ($C_1$-$C_4$)alcohol. The duration of the alcoholic activation period can be relatively short, e.g., one, five, or ten, to about 30 minutes under certain conditions, or it can be extended for several hours, for example 1-3 hours, or more.

The ester can be a $C_{10}$-$C_{24}$ fatty acid ester. In another embodiment, the ester can be a $C_{16}$-$C_{24}$ fatty acid ester. The alkyl chain of the $C_{10}$-$C_{24}$ fatty acid ester or $C_{16}$-$C_{24}$ fatty acid ester can be saturated or it can have one or more sites of unsaturation or epoxidation. In another embodiment, the fatty acid ester has 1, 2, 3, or 4 sites of unsaturation, epoxidation, or a combination thereof.

Any variety of esters can be transesterified with the catalyst of the invention. The catalyst works well at transesterifying glyceride esters. The glyceride ester can be a mono-, di-, or tri-ester of glycerol. In one specific embodiment, the ester is a triglyceride.

Any variety of alcohols can be used to replace the alkanol portion of the ester that is transesterified. The alcohol is typically a ($C_1$-$C_4$)alcohol. The ($C_1$-$C_4$)alcohol can be methanol or ethanol. In other embodiments, the ($C_1$-$C_4$)alcohol can be propanol, iso-propanol, butanol, iso-butanol, sec-butanol, or a combination thereof.

One advantage of the catalyst described herein is that besides the alcohol used to esterify or transesterify a compound, no other solvent is required. Thus, the formation of the product ester (e.g., biodiesel) can be carried out without added solvent. In other embodiments, an organic solvent can be added to alter the solubility, viscosity, or other properties of the starting oil. Such solvents include ethereal solvents such as ethyl ether, tetrahydrofuran, or dioxane; hydrocarbon solvents such as pentane or hexane; ketones such as acetone or t-butyl methyl ketone; or a combination thereof.

After the catalyst is prepared, the particles can be recovered from the reaction mixture by a variety of techniques, including decanting or filtering, such as through a sintered glass funnel. The catalyst can maintain catalytic activity after more than five times of using and recovering the catalyst. In certain embodiments, the can maintain catalytic activity after more than ten times, more than sixteen times, or more than twenty times of using and recovering the catalyst.

Kiln dust acts as an efficient catalyst with not only vegetable oils, but also with oils with high free fatty acid contents, which is a significant problem with most currently known esterification and transesterification catalysts. High free fatty acid content oils include chicken fats and used cooking oils.

Advantages of using kiln dust as a catalyst include that it is an insoluble heterogeneous catalyst that can be easily separated from a reaction mixture without washing or neutralization. The catalyst material is easily recycled for use in subsequent catalytic reactions. The material for the catalyst system is derived from waste that is generated from cement production, thus the catalyst is widely available and typically available at no cost. The activation process is extremely low in cost. The catalyst material is stable, even after repeated use as a catalyst in reactions. Finally, the catalyst is highly active, producing biodiesel from oils rapidly (often in less than one hour) and under mild conditions.

Examples of the catalyst activation process include the following methods. One method to activate the catalyst for a batch reaction includes suspending the catalyst in an alcohol (e.g., methanol) before adding the feedstock oil. Stirring the suspension can improve the activation. The stirring can be carried out for about 20 minutes, about 30 minutes, about 1 hour, or overnight (about 8-12 hours). Typically, at least about 20 minutes of stirring provides suitable activation of the catalyst. Another method includes impregnating the catalyst in methanol without stirring but with some agitation, such as shaking, periodically during the activation period. This activation procedure can be carried out, for example, for at least about 20 minutes. Both methods have provided suitably activated catalyst systems. Activation for a continuous process could be carried out by flushing the catalyst with fresh alcohol for a period of time prior to contacts with a subsequent amount of feedstock, optionally with agitation and/or heating.

Even after catalyst activity declines, for example, after about 15-20 reaction cycles, the catalyst can still be regenerated. A catalyst regeneration process can be carried out as follows. The recyclability test showed that the catalyst could be reused numerous times. After a certain number of cycles (e.g., greater than 15-20), the catalyst may provide less reactivity. At some point the catalyst may become substantially inactive. It was found that catalyst with reduced activity could be regenerated to full activity by calcination at suitable temperatures.

The biodiesel that can be produced by the methods described herein is increasingly becoming a viable biodegradable alternative to petroleum-based fuels. The by-product of the reaction, glycerol, has a variety of cosmetic and food uses, and is also under investigation as a biodegradable alternative to petroleum-based ethylene glycol and propylene glycol for various application, such as in aviation de-icing formulations. Additionally, the kiln dust catalyst system is more easily separated from biodiesel reaction mixtures than the commonly used calcium oxide, allowing for significantly greater recycling of catalyst and more economical production costs for the biodiesel.

Methods of Catalysis

The utilization of kiln dust as catalyst for biodiesel production not only provides a very active, reusable heterogeneous catalyst, but also provides an application for this solid that would otherwise be disposed in landfills, creating environmental issues and economical burden for the cement companies.

It has been demonstrated that CKD, a waste product from cement production, can serve as a highly active heterogeneous catalyst for the transesterification reactions of various glycerides and oils, including soybean oil. Additionally, CKD can serve as a highly active heterogeneous catalyst for the esterification reactions of various fatty acids, glycerides, fats, and oils, including free fatty acids and animal fat compositions. The reactivity and recyclability of this heterogeneous solid catalyst system has been investigated. For example, CKD can catalyze the transesterification reaction of soybean oil to methyl soyate (biodiesel) at about 65° C. in refluxing methanol with 100% yield in about 2 hours. The catalyst can be recycled and reused more than 16 times without any purification. Also, it has been discovered that, combined with solid acid catalysts and/or molecular sieves, CKD can efficiently convert poultry fat to biodiesel under a mild reaction condition. Lime kiln dust (LKD) can provide catalytic activity similar, and sometimes superior to, that of CKD.

The biodiesel production process can be illustrated as below in Scheme 1. Whereas many currently known base catalysts are destroyed by free fatty acids, the kiln dust catalyst system can conveniently convert even animal fats and various restaurant oils directly to biodiesel when in the presence of an alcohol simply by adding an acid, such as a solid acidic particle, for example, an acidic mesoporous aluminum silicate mixed oxide. The use of drying agents such as molecular sieves can also help facilitate the esterification or transesterification reactions, in addition to helping to preserve the recyclability of the catalysts.

difficulty in the separation and purification of the biodiesel produced. The use of kiln dust avoids this problem because the kiln dust catalytic activity is not negatively affected by the free fatty acids and in fact can be used to esterify such free fatty acids prior to transesterification of the animal or vegetable oils, as described in the Examples below.

The following Examples are intended to illustrate the above invention and should not be construed as to narrow its scope. One skilled in the art will readily recognize that the Examples suggest many other ways in which the present invention could be practiced. It should be understood that many variations and modifications may be made while remaining within the scope of the invention.

EXAMPLES

General Description of Materials

Cement kiln dust raw materials were obtained from several commercial cement suppliers, including Lehigh Cement Company, Lafarge Corporation, Holcim Inc., and St. Mary's Cement Inc., among others. Methanol was purchased from Fisher and was used as received, unless otherwise stated. Anhydrous methanol was obtained from a solvent purification system that included an alumina column (Pure Solv MD-5). Molecular sieve 4A was purchased from Fisher and was used for dehydration of liquids. Molecular sieves were re-activated at 150° C. under vacuum for 4-5 hours after initial use. De-gummed soybean oil was obtained from West Central Co-op (Iowa). Two types of chicken fat were investigated, one from West Central Co-op (Iowa), denoted as PF(I) and the other donated by a farm in Iowa, referred to as PF(II). Portland Cement was Holcim, Type 1, Type GU. Nanopure water (18.1 MHz) was obtained by passing laboratory distilled water through a Barnstead E-pure water purification system.

Example 1

Soybean Oil Transesterification by Cement Kiln Dust (CKD)

A typical procedure for the transesterification reaction was as follows. Methanol (180 mL, 4.44 mol) was added to 0.3 g Scheme 1. Biodiesel Production Schematic

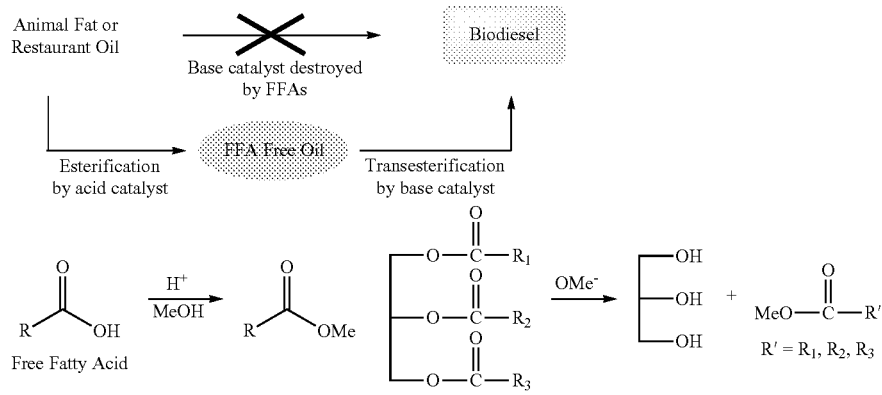

For the transesterification of animal and vegetable oils with high free fatty acid content, schematically illustrated in Scheme 1, the use of alkaline catalysts such as sodium hydroxide is undesirable because of the formation of relatively large amounts of soaps, leading to product loss and of cement kiln dust catalyst, and the resulting suspension was stirred for 30-40 minutes under refluxing conditions to activate the catalyst. Soybean oil (6.9 g, 7.9 mmol) was then added to the catalyst composition mixture, and the reaction was stirred under refluxing conditions (~64.7° C.) for 30 minutes. The weight percentage of solid catalyst to oil was 4.3 and the volume ratio of methanol to oil was 24. Sample aliquots were withdrawn from the reaction mixture at various time intervals. The aliquots were analyzed by $^1$H NMR in CDCl$_3$. After the reaction was complete, the reaction mixture was filtered through a glass frit and rinsed with a minimal amount of methanol. ICP-MS analysis showed that the crude product mixture (biodiesel, glycerin, and methanol) contained about 20-140 ppb of calcium ions. The final product of biodiesel and glycerin was isolated from the filtrate by removing any remaining methanol under reduced pressure.

Yield Determination:

The esterification conversion percentage was determined by $^1$H NMR analysis. NMR spectra were obtained in CDCl$_3$. The conversion was calculated by determining the ratio of methylene hydrogens, positioned at ~2.3 ppm, to methyl protons, positioned at ~3.6 ppm. As conversion proceeds, the characteristic peaks (~3.7-4.2 ppm) of the triglyceride backbone disappear.

To achieve essentially complete conversion of the soybean oil to biodiesel and glycerol, CKD-5 and CKD-BP catalysts required only 30 minute and 15 minute reaction times, respectively (see FIG. 1). However, CKD-ESP showed almost no reactivity under these reaction conditions.

Activation Effectiveness:

CKD catalysts were stirred in methanol before adding the feedstocks. Results showed that less than 10% yields were obtained when feedstocks were added simultaneously with CKD catalyst, whereas a 100% yield was obtained when the catalysts were activated by stirring in methanol at 64.7° C. for 30 minutes. This observed difference in reactivity can be attributed to the benefit of having the solid catalyst evenly suspended in methanol, potentially to provide a high area of contact. The surface of CKDs may also benefit from being activated by first associating with methanol.

Example 2

Effects of Relative Methanol Quantity

Figure 2:
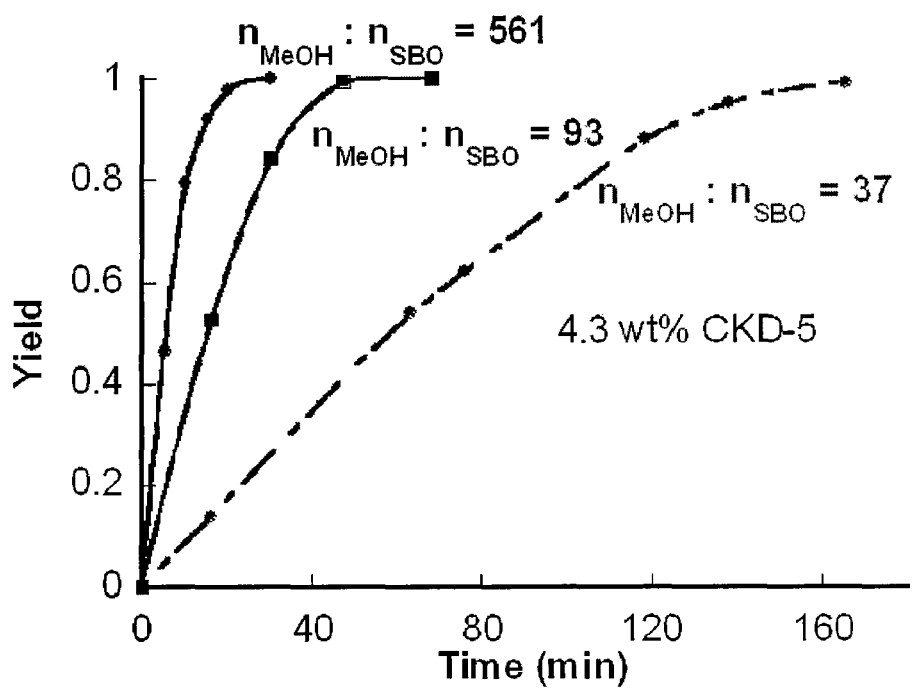
FIG. 2 illustrates the effect of various amounts of methanol on the conversion of soybean oil to biodiesel, according to one embodiment.

CKD-5 was used as the catalyst in this Example. FIG. 2 illustrates the effect of the amount of methanol in the biodiesel production reaction. As shown in FIG. 2, use of higher amounts of methanol resulted in a faster reaction. The overall reaction was complete in 30 minutes when the molar ratio of MeOH to soybean oil ("SBO") was set at 561. However, 1.25 hours and 3 hours were required to obtain 100% conversion when the molar ratio $n_{MeOH}$:$n_{SBO}$ was 93 and 37, respectively. Despite a slower reaction with lower methanol ratios, the molar ratio $n_{MeOH}$:$n_{SBO}$=37 was used as a standard procedure to evaluate the potential of this reaction under highly economical conditions (e.g., lower methanol loading).

2.1. CKD Catalyzed Biodiesel Production of Soybean Oil: 561 eq. MeOH.

Cement kiln dust (CKD-5) (0.3 g) was added to 180 mL of methanol, and the mixture was stirred at 65° C. to uniformly disperse the catalyst. After stirring about 30 minutes, 7.5 mL of soybean oil was introduced and the reaction mixture was stirred at 65° C. The conversion of soybean oil to methyl esters (biodiesel) was complete in 30 minutes. The crude product mixture was filtered through a glass-fritted funnel and the product-containing filtrate was evaporated under vacuum to remove methanol. The yield of methyl esters (biodiesel) was analyzed by $^1$H NMR.

2.2. CKD Catalyzes Biodiesel Production of Soybean Oil: 93 eq. MeOH.

Similar to the procedure above, cement kiln dust (CKD-5) (0.4 g) was added to 40 mL of methanol, and the mixture was stirred at 65° C. After about 40 minutes, 10 mL soybean oil was introduced and the reaction was stirred at 65° C. The reaction reached 100% yield in 1.25 hours.

2.3. CKD Catalyzes Biodiesel Production of Soybean Oil: 37 eq. MeOH.

Cement kiln dust (CKD-5) (0.8 g) was stirred in 32 mL of methanol at 65° C. for about 40 minutes. Soybean oil (20 mL) was introduced and the reaction mixture was stirred at 65° C. The transesterification reaction was found to be complete in 3 hours.

Example 3

Recyclability Tests of the Cement Kiln Dust (CKD) Catalyst

Figure 3:
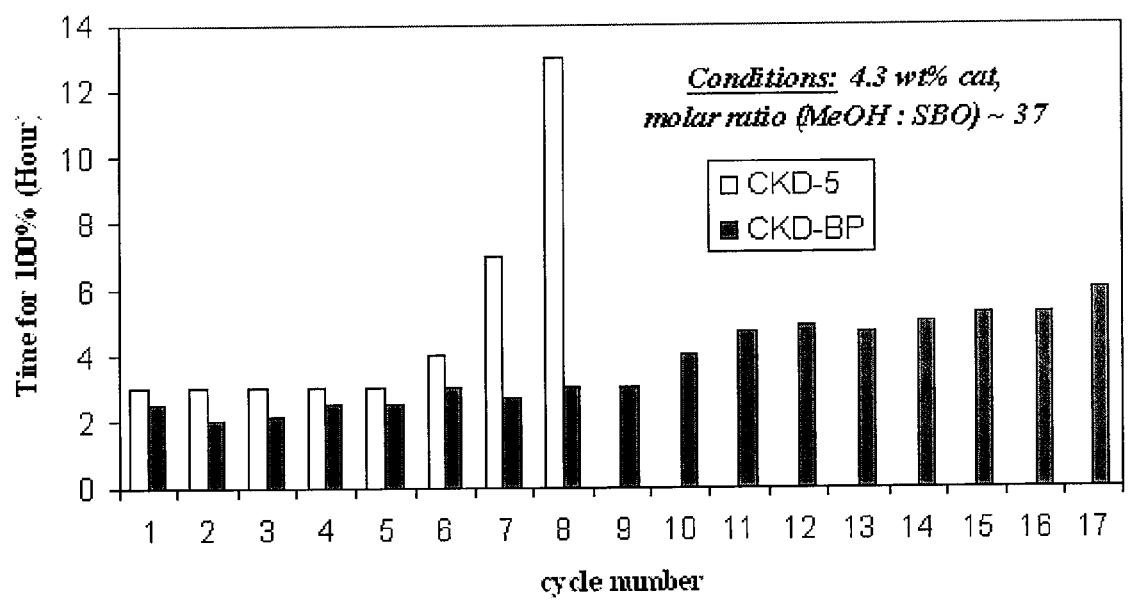
FIG. 3 illustrates a recyclability study of CKD-5 and CKD-BP, according to one embodiment. Reaction conditions: 1.2 g of a CKD catalyst in 48 mL MeOH and 30 mL soybean oil at 64.7° C.; molar ratio of MeOH to oil was 37; volume ratio of MeOH to oil was 1.6.
Figure 4A:
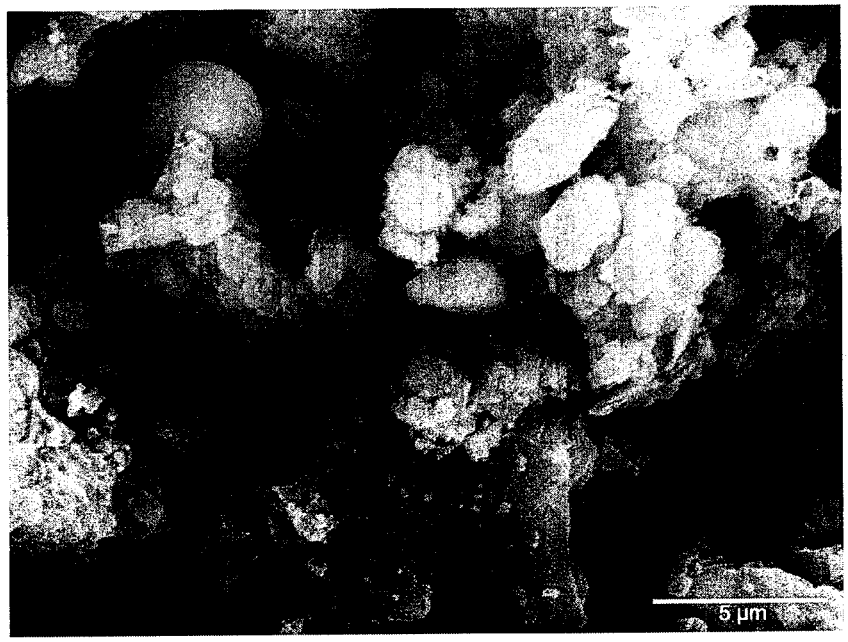
FIG. 4 shows scanning electron micrographs (SEM) of the CKD catalysts, according to one embodiment. An amorphous, disordered structure is observed with the CKD-5 sample, and more spherical morphologies with fine particles are demonstrated for the CKD-BP sample. (a) CKD-5 (5,000×); (b) CKD-BP (5,000×); (c) CKD-BP (50,000×); (d) CKD-BP after 17 cycle reactions (5,000×).
Figure 4B:
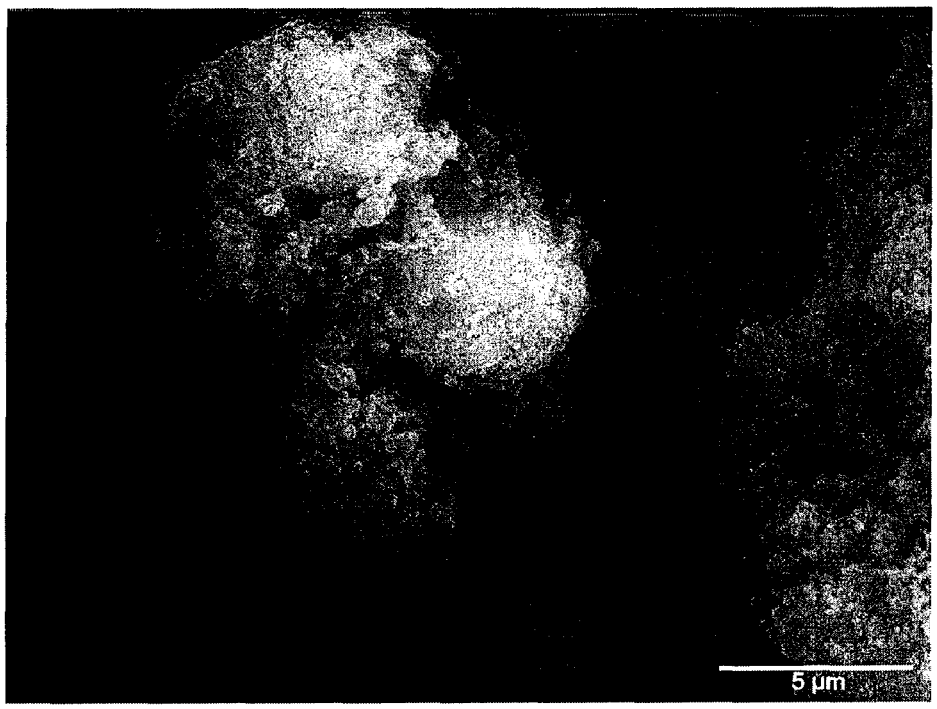
Figure 4C:
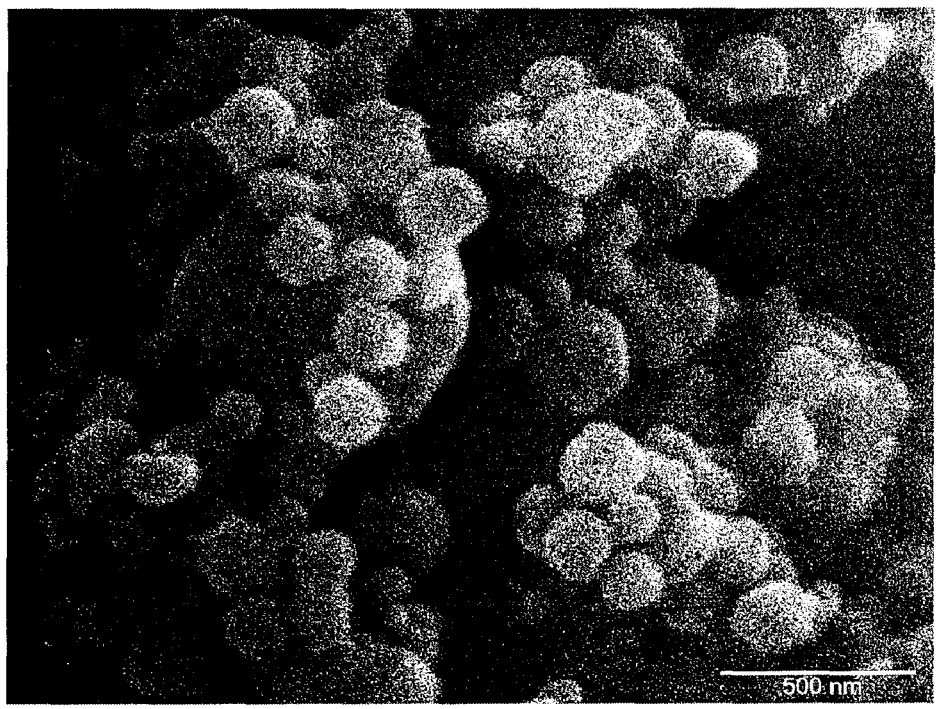
Figure 4D:
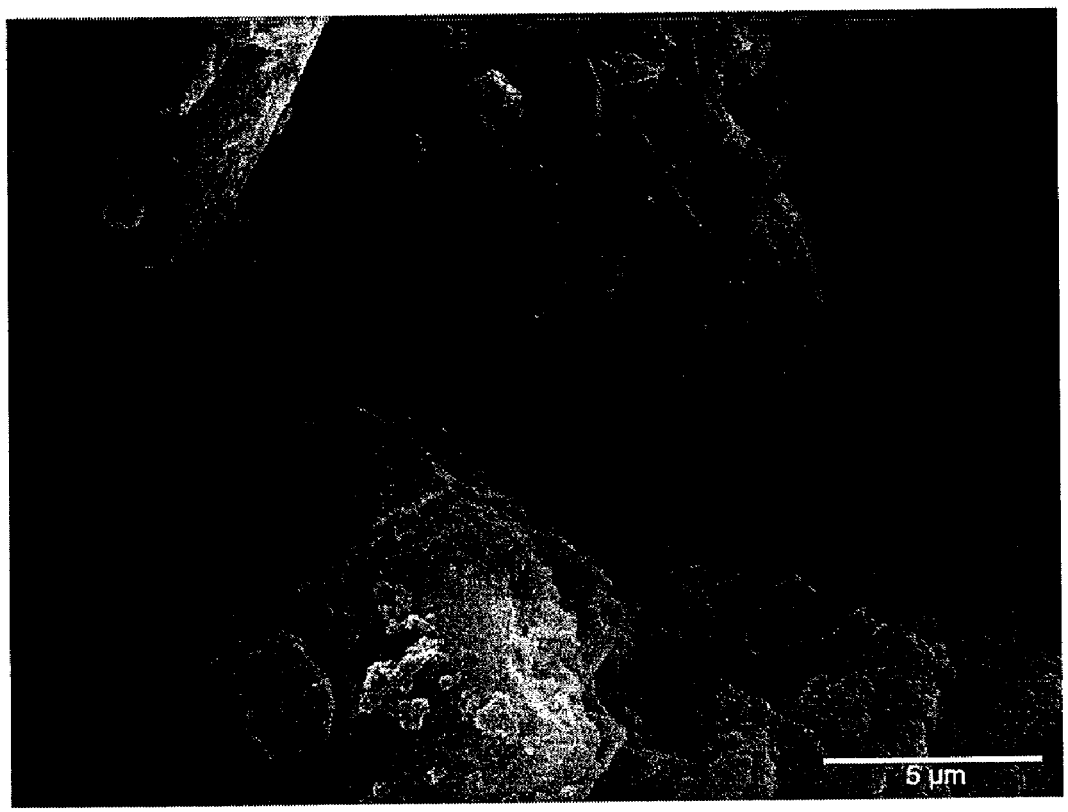

An important advantage of using heterogeneous materials as catalysts is the ability to recycle and reuse the solid catalyst. Catalyst recycling was achieved by simple filtration of the mixture at the end of the reaction. The recovered catalyst was used again under the same reaction conditions without any purification. The catalyst CKD-BP could be reused up to 17 times for soybean oil transesterification reaction (FIG. 3). Remarkably, there was no significant loss of activity in each successive reaction. Due to different chemical components and microstructure, CKD-5 can be reused up to 8 times for soybean oil transesterification reactions under same conditions. In comparison with the recyclability of other solid metal oxide catalysts, the CKD catalysts showed an unprecedented stability and recyclability for biodiesel synthesis.

For a typical example, 1.2 g cement kiln dust (CKD-5) was added to 48 mL methanol, and the mixture was stirred at 64.7° C. After about 40 minutes, 30 mL soybean oil was introduced and the reaction achieved 100% yield in 2.5 hours at 64.7° C. Liquid samples were withdrawn from the reaction mixture at different time intervals to monitor the conversion. The aliquots were analyzed by $^1$H NMR in CDCl$_3$. The solid catalyst was filtered through a fine glass-fritted funnel (pore size 4-5.5 nm) and then was transferred back to the original reaction flask. Another 48 mL fresh methanol was recharged to the catalyst and the methanol/catalyst mixture was pre-activated for 40 minutes under refluxing methanol temperature before adding 30 mL soybean oil. The second cycle reaction finished in 2 hours without losing any reactivity. The same procedure was applied for each reaction cycle. After 9 cycles, the reaction slowed somewhat, which may be due to the loss of some catalyst in the filtration and transfer steps on the small scale of these reactions.

Example 4

Catalytic Performances of CKD Catalyst Under Dry Conditions

In this experiment, anhydrous methanol and dried soybean oil were used. The catalyst was used without any purification. Anhydrous methanol was obtained from a solvent purification system that included an alumina column (Pure Solv MD-5). Soybean oil was dried by contact with molecular sieve 4 Å for 8-12 hours. The reaction system was purged of air by passing a stream of nitrogen gas through the system, and the system was then closed during the reaction to isolate from moisture.

A typical procedure was as follows: 0.4 g cement kiln dust (CKD-BP) was added to 16 mL anhydrous methanol. The mixture was stirred at 64.7° C. for 40 minutes. The predried soybean oil (10 mL) was introduced to the catalyst-methanol mixture. The molar ratio of MeOH and soybean oil was equal to 37, and the volume ratio was 1.6. After stirring at 64.7° C. for 1 hour, the soybean oil was found to have been completely converted to methyl esters (biodiesel). After the reaction, the crude product mixture was filtered through a fine glass-fritted funnel (pore size 4-5.5 nm) and the product-containing filtrate was evaporated under vacuum to remove methanol. The liquid products were added to a separation funnel to separate the methyl ester and the glycerol byproduct. The yield of methyl esters was analyzed by $^1$H NMR.

Employing the dry conditions demonstrated that the reaction could be run with significantly lower amounts of methanol. For example, the reaction can be run with only 12 molar equivalents of methanol. 0.4 g cement kiln dust (CKD) was added to 5 mL anhydrous methanol. The mixture was stirred at 64.7° C. for 40 minutes. The pre-dried soybean oil (10 mL) was introduced to the catalyst methanol mixture, where the molar ratio of MeOH and soybean oil was 12, and volume ratio was 0.5. The reaction required only about 1.5 hours to achieve complete conversion. The yield of methyl esters was analyzed and confirmed by $^1$H NMR. The results are summarized in Table 1.

TABLE 1

Catalytic performance of the cement kiln dust (CKD-BP) catalyst under dry conditions with various amounts of methanol.

| Feedstock | Catalyst % | Molar ratio of methanol to oil | Volume ratio of methanol to oil | Reaction condition (T/P) | Time for full conversion (hours) |
|---|---|---|---|---|---|
| Soybean oil | 4.3% | 37 | 1.6 | 64.7° C./1 atm | 1 |
|  | 4.3% | 12 | 0.5 | 64.7° C./1 atm | 1.5 |
|  | 4.3% | 6 | 0.25 | 64.7° C./1 atm | 3 (~95%) |

Example 5

Temperature and Pressure Effects on Biodiesel Production of Soybean Oil Using CKD as a Catalyst High temperature/pressure reactions were carried out in a 100 mL Parr Series 4560 Mini Bench Top autoclave reactor. The reactor was magnetically stirred. The elevated pressure was a result of the vapor pressure of methanol at the reaction temperature.

It was demonstrated that the kinetics of the reaction were significantly enhanced by increasing temperature and pressure. In a typical reaction, 0.4 g cement kiln dust (CKD) was mixed with 5 mL anhydrous methanol in an autoclave reactor at 64.7° C. for 40 minutes. Dry soybean oil (10 mL) was introduced to the catalyst/methanol mixture. The complete conversion of soybean oil to biodiesel was found to be complete in 30 minutes at 120° C. and 90 psi. After cooling the reactor, the crude product mixture was filtered through a fine glass-fritted funnel (pore size 4-5.5 nm) and the product-containing filtrate was evaporated under vacuum to remove methanol. The quantitative conversion of soybean oil to methyl esters was confirmed by $^1$H NMR.

Example 6

Poultry Fat Esterification Using CKD Catalyst Under Dry Conditions

Dry methanol (30 mL, 0.74 mol) was added to the CKD-BP catalyst (0.2 g) and molecular sieve 4 Å (8 g), and the resulting solution was stirred for 30 minutes at 50° C. before adding dry poultry fat PF(I) (1 mL). In this reaction, the weight percentage of solid catalyst to oil was 22 and the volume ratio of methanol to oil was 30. Molecular sieve 4 Å adsorbed $H_2O$ that was produced in the reaction. The reaction mixture was filtered through a glass frit and rinsed with a minimal amount of methanol. The final product was isolated from the filtrate by evaporating methanol under vacuum. $^1$H-NMR measurements showed that the reaction was complete in 10 hours.

Example 7

CKD Catalyzed Biodiesel Production from Free Fatty Acid (FFA) Containing Oil Feedstocks Under Elevated Temperature and Pressure All reactions were carried out in a 100 mL Parr Series 4560 Mini Bench Top autoclave reactor. The reactor was magnetically stirred. The pressure was a result of the vapor pressure of methanol at the reaction temperature. The feedstocks investigated were 15 wt. % oleic acid containing soybean oil (about 13 wt. % acid by titration), chicken fat (PF(I) and PF(II)), and used cooking oil.

Oleic acid containing soybean oil was obtained by simply dissolving 15 g of oleic acid into 85 g soybean oil. The mixture was then dried by molecular sieve 4 Å for 8-12 hours. 0.6 g cement kiln dust (CKD) and 15 mL anhydrous methanol were added to an autoclave reactor and pre-activated at 64.7° C. for 40 minutes. Dry oleic acid-containing soybean oil (15 mL) was introduced and the reaction was carried out at 130° C. in a closed system. The pressure reached about 100 psi. The reaction was found to be complete in 2.5 hours. After cooling the reactor, the crude product mixture was filtered through a fine glass-fritted funnel (pore size 4-5.5 nm) and the product-containing filtrate was evaporated under vacuum to remove methanol. The yield of methyl esters was analyzed and complete conversion was confirmed by $^1$H NMR.

Chicken fat (PF(I)) was used after drying via molecular sieve 4A. Chicken fat PF(II) was filtered first to remove solid particles and then heated to 90° C. under vacuum to reduce water content. The liquid portion was further dried by molecular sieve 4 Å overnight. For a typical experiment, 0.6 g cement kiln dust (CKD-BP) and 15 mL anhydrous methanol were added to an autoclave reactor and pre-activated at 64.7° C. for 40 minutes. Dry chicken fat (15 mL) was introduced and the reaction was carried out at 130° C. in a closed system. The pressure reached about 100 psi during the reaction. The reaction was found to be complete in 2.5 hours. After cooling the reactor, the crude product mixture was filtered through a fine glass-fritted funnel (pore size 4-5.5 nm) and the product-containing filtrate was evaporated under vacuum to remove excess methanol. The yield of methyl esters was analyzed and complete conversion was confirmed by $^1$H NMR.

Used cooking oil was obtained from a local restaurant. The cooking oil included deep fried canola oil with about 0.2% free fatty acids (FFA) and about 5% protein impurities. The oil was dried by molecular sieve 4 Å for 8-12 hours. 0.4 g cement kiln dust (CKD) and 5 mL anhydrous methanol were added to an autoclave reactor and pre-activated at 64.7° C. for 40 minutes. Dry used cooking oil (10 mL) was introduced and the reaction was carried out at 120° C. in a closed system. The pressure reached about 90 psi during the reaction. The reaction was found to be complete in 35 minutes. After cooling the reactor, the crude product mixture was filtered through a fine glass-fritted funnel (pore size 4-5.5 nm) and the product-containing filtrate was evaporated under vacuum to remove methanol. The yield of methyl esters was analyzed and complete conversion was confirmed by $^1$H NMR. The results are summarized in Table 2.

TABLE 2

Result summary of biodiesel production from investigated feedstocks.

| Feedstock | Catalyst % | Volume ratio of methanol to oil (molar ratio) | Reaction condition (T/P) | Time for full conversion |
|---|---|---|---|---|
| Soybean oil | 4.3% | 0.5 (12) | 120° C./90 psi | 30 min |
| 15 wt. % oleic acid in soybean oil | 4.3% | 1 (24) | 130° C./100 psi | 2.5 h |
| Chicken fat PF(I) | 4.3% | 1 (24) | 130° C./100 psi | 2.5 h |
| Chicken fat PF(II) | 4.3% | 1 (24) | 130° C./100 psi | 2.5 h |
| Used cooking oil | 4.3% | 0.5 (12) | 120° C./90 psi | 35 min |

Example 8

Poultry Fat Esterification Reactions Via a 3-Step Approach: Combined Acid and Base Catalyst Additives One issue in using CKD for the conversion of poultry fat to fatty acid methyl esters (FAMEs) derives from CKD's highly basic character. CKD can be neutralized and deactivated by the free fatty acids (FFAs) in poultry fat and other FFA-containing feedstocks by a process called saponification (soap-formation). Also, water produced by the saponification may hydrolyze the CKD catalyst. To circumvent these problems, a new approach has been developed to efficiently and economically convert poultry fat to methyl esters by using a combination of catalysts, including solid acid catalysts and CKDs. The use of Al-MCM is described herein as an example of the acid catalyst, however this application is not limited to Al-MCM. Other solid acid catalysts that can be employed include zeolites, acidic Nafion resins, sulfonic-functionalized SBA or MCM materials, and the like.

An acidic mesoporous aluminum silicate mixed oxide (Al-MCM) material was applied to poultry fat to remove FFAs. Water was removed by adding molecular sieve 4 Å into the system. CKD was then added to catalyze the biodiesel production. The following is a typical experimental procedure: Al-MCM (0.1 g) and poultry fat (1 g) were added to 10 mL of methanol and reacted for 4 hours at 65° C. Molecular sieve 4 Å was then added to the filtrate overnight to remove water. The mixture was then poured into 0.1 g CKD-BP previously activated in 3 mL of methanol. The reaction was found to be complete in 1 hour at 65° C.

Example 9

Portland Cement as a Transesterification Catalyst

Because the chemical composition of Portland cement is similar to that of kiln dusts, the catalytic performance of Portland cement was evaluated by following an experimental procedure similar to the procedures outlined above. The reaction flask was charged with 0.3 g Portland cement and 180 mL of methanol, and this mixture was allowed to stir for 30 minutes to create an even suspension. Soybean oil (7.5 mL) was added and the reaction mixture was stirred under reflux for 24 hours to afford complete conversion. Under dry condition where anhydrous methanol was applied and soybean oil was dried by molecular sieve 4A for overnight, this reaction reached completion in 40 minutes. The Portland cement could be filtered off and recycled in 2-3 further reaction cycles before losing substantial catalytic activity.

Example 10

Soybean Oil Transesterification by Lime Kiln Dust (LKD)

Methanol (120 mL, 2.96 mol) was added to 0.2 g of lime kiln dust, and the resulting suspension was stirred for 30 minutes at 64.7° C. to provide the activated catalyst composition. Soybean oil (4.6 g, 5.28 mmol) was then added to the catalyst composition, and the reaction mixture was stirred under refluxing conditions for 30 minutes. The weight percentage of solid catalyst to oil was 4.3 and the volume ratio of methanol to oil was 24. Analysis of the product showed 90% of conversion after only 16 minutes. The conversion of soybean oil to fatty acid methyl esters (FAME) was complete in 30 minutes.

Example 11

Structural Analysis of CKD

Nitrogen Adsorption Analysis:

The surface area of the CKD materials was determined by nitrogen adsorption-desorption surface analysis. Results show that CKD samples have low surface areas (about 2-3 $m^2 \cdot g^{-1}$).

Electron Microscopy:

Scanning electron microscopy (SEM) was performed on the CKD catalysts to determine the morphology and to analyze the porous structure of the catalysts. The SEM spectra, FIG. 4, establish that CKD-5 and CKD-BP have different morphologies. CKD-5 has an amorphous structure with larger particle size, whereas CKD-BP samples exhibited more ordered, spherical morphologies and fine particles.

Example 12

CKD Analytical Data

Classification of CKD Samples

The composition and mineralogy of CKD is dependent on the raw materials used, the type of kiln used in the cement production, and individual plant practices, such as operating temperatures, fuel types, dust collection systems, and the like. CKD typically contains calcite, lime, quartz, alkali chlorides and sulfates. Three CKDs (denoted as CKD-BP, CKD-ESP, and CKD-5) were analyzed as follows.

To analyze the chemical composition and the mineralogical composition of the CKD samples, two different spectroscopic methods were employed. X-ray fluorescence (XRF) spectrometry was used to determine the presence and the quantity of the individual elements in the CKD samples. In a typical experiment, a standard fusion technique was applied to dissolve or decompose solid samples using a flux to yield a homogeneous glass. This process eliminated the inhomogeneity of different particle sizes and mineralogical effects. Next, X-ray powder diffraction (XRD) spectra of these materials were obtained to identify their phase composition.

The differences in the chemical composition of 63 different freshly produced CKD samples have been examined and reported in the literature (*Engineering Geology* 2006, 85, 165). The percent ranges of different chemical elements are represented in the form of the corresponding oxides and the results are summarized in Table 3. Among these CKDs, 58 samples were obtained from different cement factories located in the United States. The different oxides outlined in Table 3 were generated from the oxidation of the fresh CKD samples.

TABLE 3

Chemical Compositions of Cement Kiln Dust

|  | Mean (wt %) | Max (wt %) | Min (wt %) |
|---|---|---|---|
| $SiO_2$ | 15.05 | 34.30 | 2.16 |
| $Al_2O_3$ | 4.43 | 10.5 | 1.09 |
| $Fe_2O_3$ | 2.23 | 6.00 | 0.24 |
| CaO | 43.99 | 61.28 | 19.40 |
| $Na_2O$ | 0.69 | 6.25 | 0.00 |
| $K_2O$ | 4.00 | 15.30 | 0.11 |
| MgO | 1.64 | 3.50 | 0.54 |
| $SO_3$ | 6.02 | 17.4 | 0.02 |
| LOI | 21.57 | 42.39 | 4.2 |
| Free CaO | 6.75 | 27.18 | 0.00 |
| Total alkali | 3.32 | 11.42 | 0.14 |
| TRO | 21.49 | 56.08 | 1.86 |

LOI: loss on ignition
TRO: total reactive oxide content = [CaO + MgO − LOI] − [$K_2O$ + $Na_2O$]
Total alkali = $Na_2O$ + 0.658 $K_2O$ Elemental Analysis and X-Ray Powder Diffraction Analysis of CKD Samples Results of the chemical analysis of cements are commonly expressed in terms of oxide components. Table 4 shows the chemical compositions of three CKD catalysts (CKD-BP, CKD-5, and CKD-ESP) that were investigated for various transesterifications of oils to biodiesel.

TABLE 4

XRF analysis of CKD-BP, CKD-5 and CKD-ESP (% by weight)

|  | CKD-BP | CKD-5 | CKD-ESP |
|---|---|---|---|
| $SiO_2$ | 12.3 | 11.5 | 8.1 |
| $Al_2O_3$ | 3.9 | 4.4 | 3.7 |
| $Fe_2O_3$ | 1.6 | 2.0 | 1.2 |
| CaO | 53.4 | 56.0 | 44.1 |
| $Na_2O$ | 1.0 | 1.0 | 0.2 |
| $K_2O$ | 7.1 | 5.9 | 0.4 |
| MgO | 1.5 | 1.3 | 1.0 |
| $SO_3$ | 15.5 | 16.7 | 2.4 |
| LOI | 3.4 | 6.0 | 38.9 |

Figure 5:
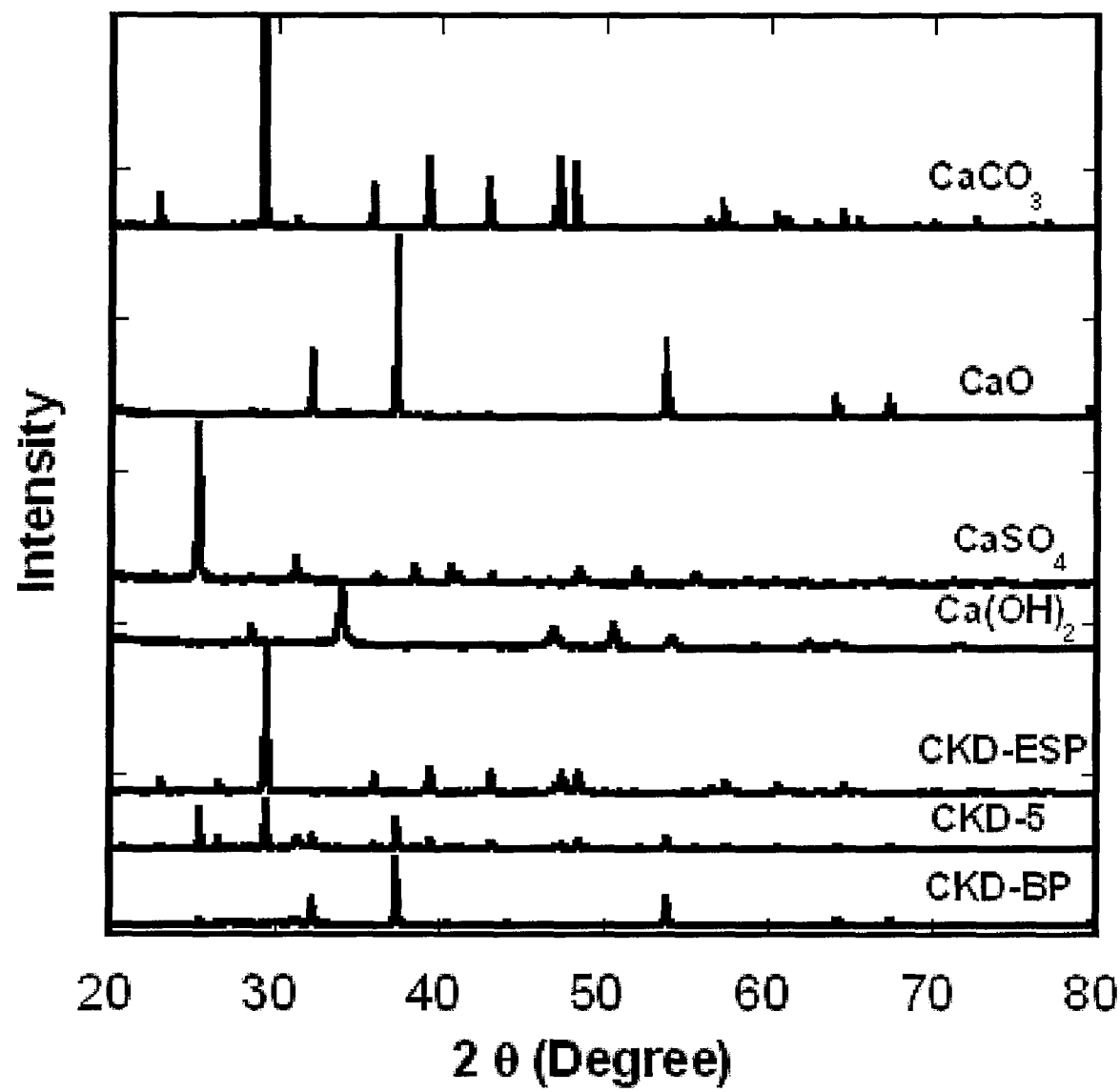
FIG. 5 shows powder XRD plots of various CKD catalysts, according to one embodiment. (a) Four calcium-containing materials (CaO, $CaCO_3$, $Ca(OH)_2$, and $CaSO_4$) and three CKD materials (CKD-BP, CKD-ESP, and CKD-5) that were evaluated as catalysts for biodiesel production. (b) CKD-5 before and after eight cycles of reactions.
Figure 5:
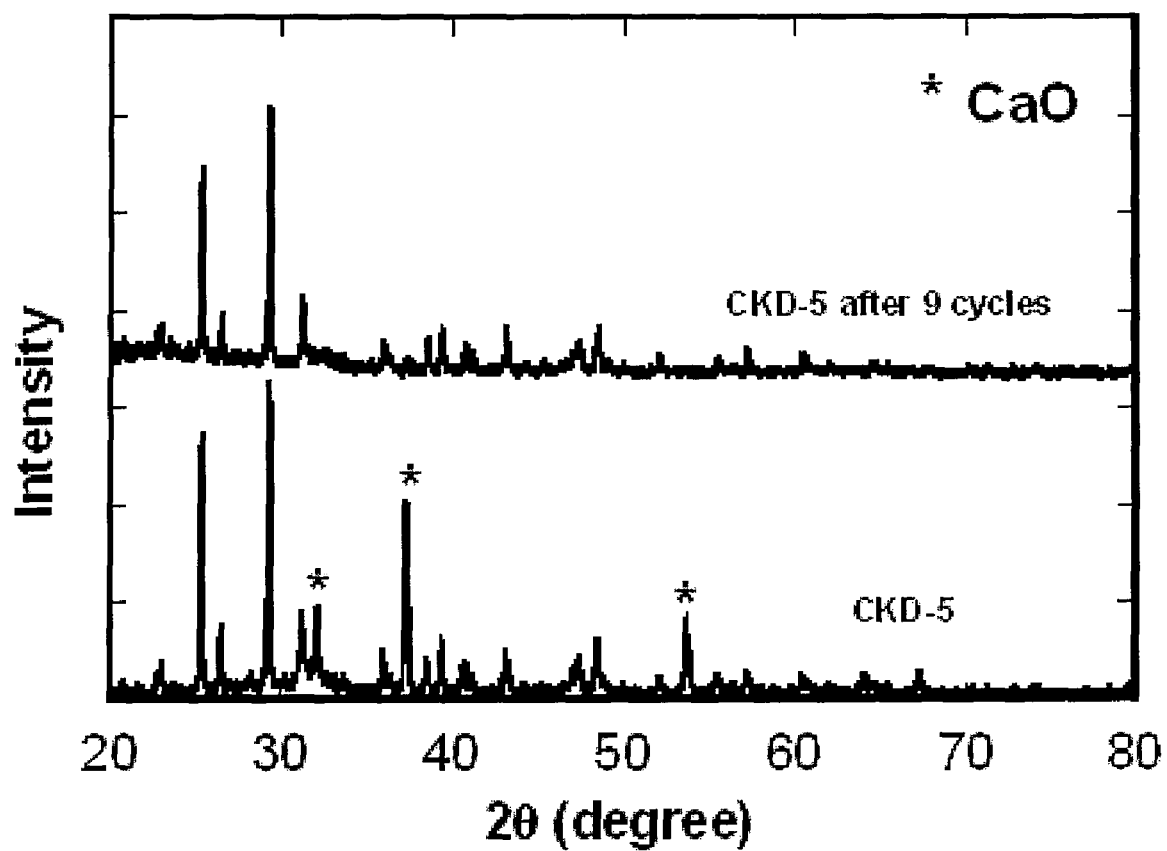

Powder X-Ray Diffraction (XRD) analyses of CKD samples are presented in FIG. 5(*a*). The major phases identified in CKD include calcium oxide (CaO), calcite ($CaCO_3$), anhydrite ($CaSO_4$), and quartz ($SiO_2$), which are also present in FIG. 5(*a*). Compared to CKD-5, CKD-BP exhibited only three major diffraction peaks around 32°, 38°, and 53° (2θ), which are assigned to calcium oxide. Thus, CKD-BP has higher amount of CaO than CKD-5 and CKD-ESP. From the reactivity study, it was found that CKDs with favorable catalytic reactivity include those that contain larger amounts of CaO (free lime), as determined by XRD analysis. For example, CKDs with greater than about 45 wt. %, or greater than about 50 wt. %, provide greater and faster conversion to products in an esterification or transesterification reaction.

Based this observation, CaO appears to be a significant component that is at least in part responsible for the high catalytic reactivity of CKD catalyst systems. This observation is further confirmed by the low catalytic reactivity of CKD-ESP material, which contains mostly $CaCO_3$ (calcite) and little or no free lime (CaO).

As shown in FIG. 5(*b*), the characteristic CaO peaks of CKDs disappeared after the transesterification reaction, which suggested that the major active species is indeed CaO. The different XRD patterns also indicated two different chemical compositions of these CKD samples obtained from different cement companies. The results show that the CKD-BP has a faster kinetic profile than CKD-5. Table 5 shows the calcined chemical composition results of various CKDs and ordinary Portland cement (Type I cement).

TABLE 5

Comparison of Calcined CKD and Portland Cement Oxide Compositions

|  | CKD-BP | CKD-5 | CKD-ESP | Portland cement |
|---|---|---|---|---|
| $SiO_2$ | 12.3 | 11.5 | 8.1 | 20.4 |
| $Al_2O_3$ | 3.9 | 4.4 | 3.7 | 5.2 |
| $Fe_2O_3$ | 1.6 | 2.0 | 1.2 | 3.6 |
| CaO | 53.4 | 56.0 | 44.1 | 64.3 |
| $Na_2O$ | 1.0 | 1.0 | 0.2 | 0.1 |
| $K_2O$ | 7.1 | 5.9 | 0.4 | 0.6 |
| MgO | 1.5 | 1.3 | 1.0 | 1.1 |
| $SO_3$ | 15.5 | 16.7 | 2.4 | 2.6 |
| LOI | 3.4 | 6.0 | 38.9 | 1.1 |

It has therefore been demonstrated that cement kiln dusts (CKDs) can serve as efficient catalysts for the conversion of organic oils to biodiesel. Combined with other acid catalysts and molecular sieves, CKDs can be used as catalysts for converting high FFA-containing oil feedstocks to the desired biodiesel methyl esters. The CKD catalysts can be easily recycled and reused without purification. Furthermore, CKDs are considered waste materials and the utilization of these solid catalysts for biodiesel production are believed to be orders of magnitude more economical than current state-of-the-art methods.

Example 13

Attempted Soybean Oil Transesterification by Non-Active Cement Kiln Dust (CKD-ESP)

Figure 6:
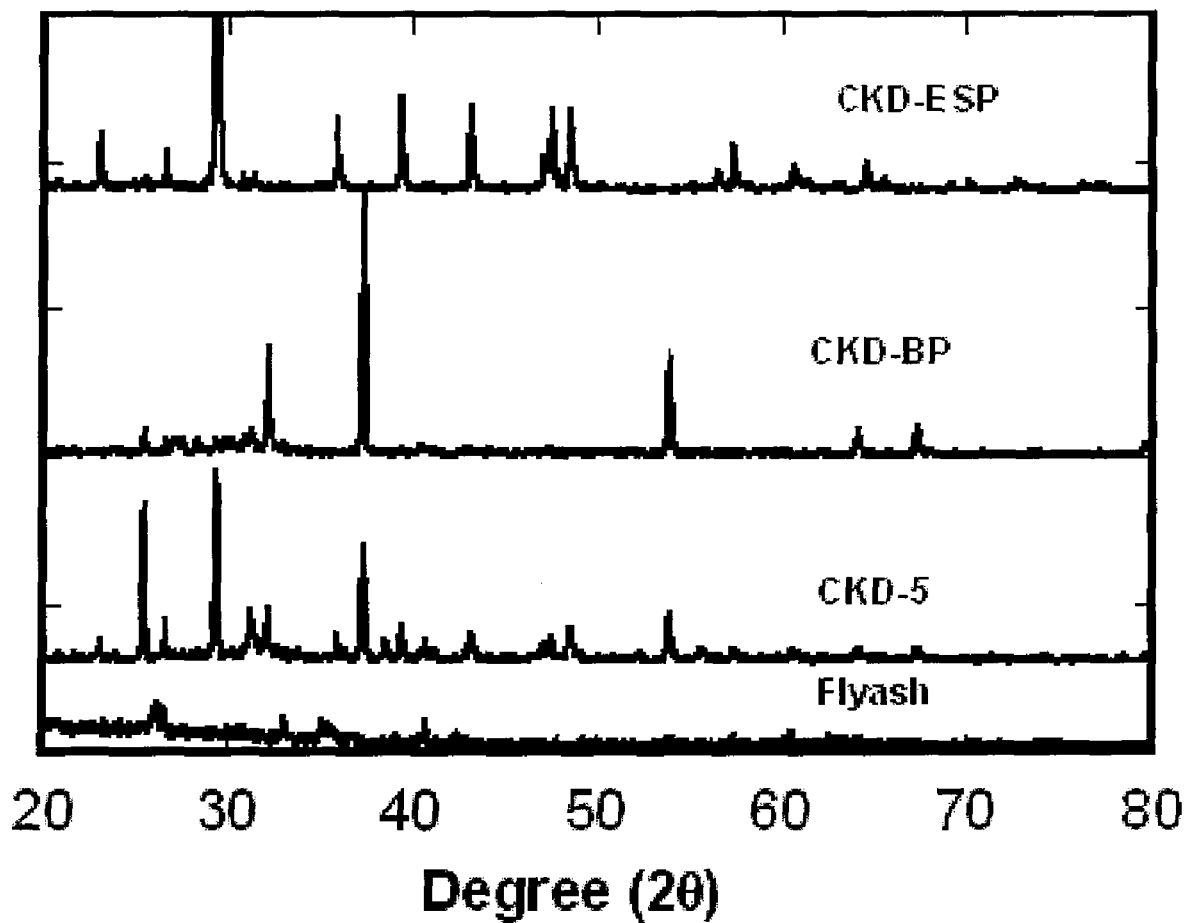
FIG. 6 shows powder XRD plots of CKD-ESP, CKD-BP, CKD-5, and fly ash. It can be observed that CKD-ESP and fly ash lack the strong CaO peaks that can be found in the CKD-BP and CKD-5 XRD plots.

Methanol (180 mL, 4.44 mol) was added to 0.3 g of cement kiln dust (CKD-ESP). The mixture was stirred for 30 minutes at 64.7° C. to disperse the solid CKD-ESP particles. Soybean oil (6.9 g, 7.9 mmol) was then added to the methanolic solution of CKD-ESP. The reaction mixture was stirred in refluxing methanol (64.7° C.) for 30 minutes. The weight percentage of solid catalyst to oil was 4.3 and the volume ratio of methanol to oil was 24. Sample aliquots were withdrawn from the reaction mixture at various time intervals to monitor the progress of the reaction. The conversion of soybean oil to FAME was analyzed by $^1$H NMR in $CDCl_3$. Over the reaction period of 6 hours, no FAME was found in the transesterification reaction using CKD-ESP as catalyst. FIG. 6 shows that CKD-ESP lacks strong calcium oxide peaks as determined by XRD analysis.

Example 14

Soybean Oil Transesterification by Fly Ash

Class-F fly ash (0.3 g) was suspended in 180 mL of methanol (4.44 mol) for 30 minutes at 64.7° C. Soybean oil (6.9 g, 7.9 mmol) was then added to the above suspension, and the reaction was carried out in refluxing methanol (64.7° C.) for 3 hours. The weight percentage of solid catalyst to oil was 4.3 and the volume ratio of methanol to oil was 24. Sample aliquots were withdrawn from the reaction mixture at various time intervals to monitor the progress of the reaction. The conversion of soybean oil to FAME was analyzed by $^1$H NMR in $CDCl_3$. No product was detected within a three hour reaction time. FIG. 6 shows that the fly ash lacks strong calcium oxide peaks as determined by XRD analysis.

Example 15

Catalytic Activity of LKD and Portland Cement

It has been demonstrated that lime kiln dusts have similar catalytic activity to cement kiln dusts, such as CKD-5, under appropriate conditions, for example, when activated by an alcohol, such as methanol. Additionally, it has been discovered that Portland cement can by used as a catalyst when employed under moisture-free conditions. By activating the Portland cement with an alcohol and carrying out the catalysis under moisture-free conditions, the catalytic activity of the Portland cement is significantly improved over non-activated conditions and/or under conditions when moisture is present. Under alcohol-activated and moisture free conditions, Portland cement shows catalytic activity and recyclability similar to CKDs. However, kiln dusts are more economic and robust than Portland cement due to the higher cost and moisture sensitivity of the Portland cement.

Example 16

Soybean Oil Transesterification by Lime Kiln Dust (LKD)

Soybean oil transesterification by LKD. A typical reaction for the transesterification of soybean oil with methanol using LKD as catalyst was carried out in an 8 liter PPI batch reactor equipped with a temperature controller and an agitator. The reactor was first charged with soybean oil (2 L) and heated to 160 degrees F. (about 71° C.) with stirring. Meanwhile, 80 g of lime kiln dust was activated in 0.5 L of methanol for 30 minutes at room temperature. The molar ratio of methanol to oil was 6 and the catalyst loading was 4.3 wt % with respect to the weight of oil. After the activation, the mixture of catalyst and methanol was added to the reactor and the reaction was carried out at 160 degrees F. with the same stirring speed. Sample aliquots were withdrawn from the reactor at various time intervals and were analyzed by $^1$H NMR in $CDCl_3$. The reaction reached 98% conversion in 90 minutes.

Soybean oil transesterification by LKD at lower temperatures. The reaction was carried out at 140, 150 and 160 degrees F. to evaluate the influence of reaction temperature. In these experiments, the molar ratio of methanol to oil was fixed at 6 and the weight percentage of catalyst to oil was 4.3. As expected, the reaction kinetics increased with temperature. For example, the conversions at 140 and 150 degrees F. were 96% in 2 hours and 98% in 1.5 hours, respectively.

Soybean oil transesterification by LKD with higher catalyst loading. In this example, 160 g of lime kiln dust (8.7 wt % catalyst loading to oil) was activated in 0.5 L of methanol for 30 minutes at room temperature (about 23° C.). Two liters of soybean oil was heated to 150 degrees F. (about 65° C.) in the reactor during the activation of catalyst. The mixture of catalyst and methanol was then charged to the reactor and the reaction was run at about 150 degrees F. with stirring. The results showed that the reaction reached 94% conversion in 1 hour and 96% in 1.5 hours.

Soybean oil transesterfication by LKD with increased molar ratio of methanol to oil. In this example, 160 g of lime kiln dust was activated in 1 L of methanol for 30 minutes at room temperature. Two liters of soybean oil was heated to 160 degrees F. in the reactor during the activation of catalyst. The molar ratio of methanol to oil was set to 12. After catalyst activation, the mixture of catalyst and methanol was charged to the reactor and the reaction was run at 160 degrees F. with stirring. The reaction reached 95% conversion in 90 minutes.

Soybean oil transesterification by different LKD samples that contain varying amounts of Ca. Two samples, LKD-18 and LKD-65, contained about 18% Ca and 65% Ca from their chemical analysis, respectively. The reactions were carried out under the following condition: 80 g of catalyst (4.3 wt %) was activated in 0.5 L of methanol (molar ratio of methanol to oil was 0.25) for 30 minutes at room temperature. After activation, the mixture of catalyst and methanol was added to the reactor and the reaction was carried out at 140 degrees F. (about 60° C.) for 2 hours. It was found that both reactions provided conversions greater than 96% in 2 hours.

Figure 7:
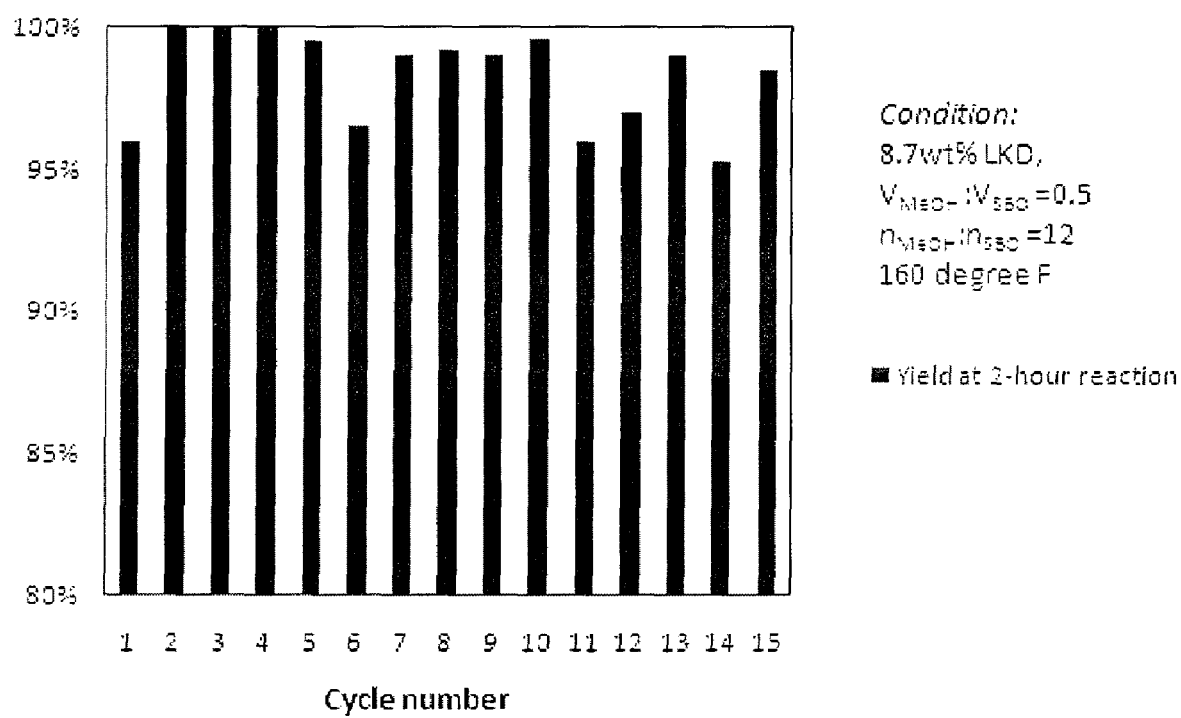
FIG. 7 illustrates a recyclability study of LKD, according to one embodiment. Reaction conditions: 8.7 wt. % LKD catalyst in methanol; ratio of methanol volume ($V_{MeOH}$) to soybean oil volume ($V_{SBO}$)=0.5; molar ratio of methanol ($n_{MeOH}$) to soybean oil ($N_{SBO}$)=12; reactions were run at 160° F. (about 71° C.). Reaction yields were measured at 2 hours.

Life cycle study of LKD for soybean oil transesterification. Catalyst recycling was achieved by simple filtration of the product mixture at the end of the reaction. The recovered catalyst was used again under the same reaction conditions without any purification. The LKD catalyst could be reused for at least 15 times without observing significant loss of reactivity (FIG. 7). The catalyst life cycle study was carried out as follows. The reactor was first charged with soybean oil (2 L) and heated to 160 degrees F. with stirring. At the same time, 160 g of lime kiln dust was activated in 1 L of methanol for 30 minutes at room temperature. After the activation, the mixture of catalyst and methanol was added to the reactor and the reaction was carried out at 160 degrees F. with the same stirring speed. In order to monitor the kinetics, sample aliquots were taken from the reactor at various time intervals and analyzed by $^1$H NMR in $CDCl_3$. Upon the completion of each reaction, the products were discharged from the reactor and the catalyst was isolated through filtration and reused for the next cycle without purification.

Chemical Composition of LKD. Similar to CKD particles, LKD particles can have variations in their chemical composition, depending on the sample. The chemical composition for two samples is provided in Table 6 below.

TABLE 6

Chemical Composition of Two Lime Kiln Dust Samples.

|  | LKD-1 (wt %) | LKD-2 (wt %) |
| --- | --- | --- |
| Free lime (free CaO) | 12.1 | 29.8 |
| $CaCO_3$ | 38.3 | 39.8 |
| MgO | 18.9 | 1.9 |
| $Al_2O_3$ | 1.2 | 4.4 |
| $Fe_2O_3$ | 0.8 | 25 |
| $SiO_2$ | 1.7 | 7.3 |
| $SO_3$ | 2.3 | 2.8 |
| LOI | 22.2 | 18.1 |

LOI: loss on ignition

Figure 8:
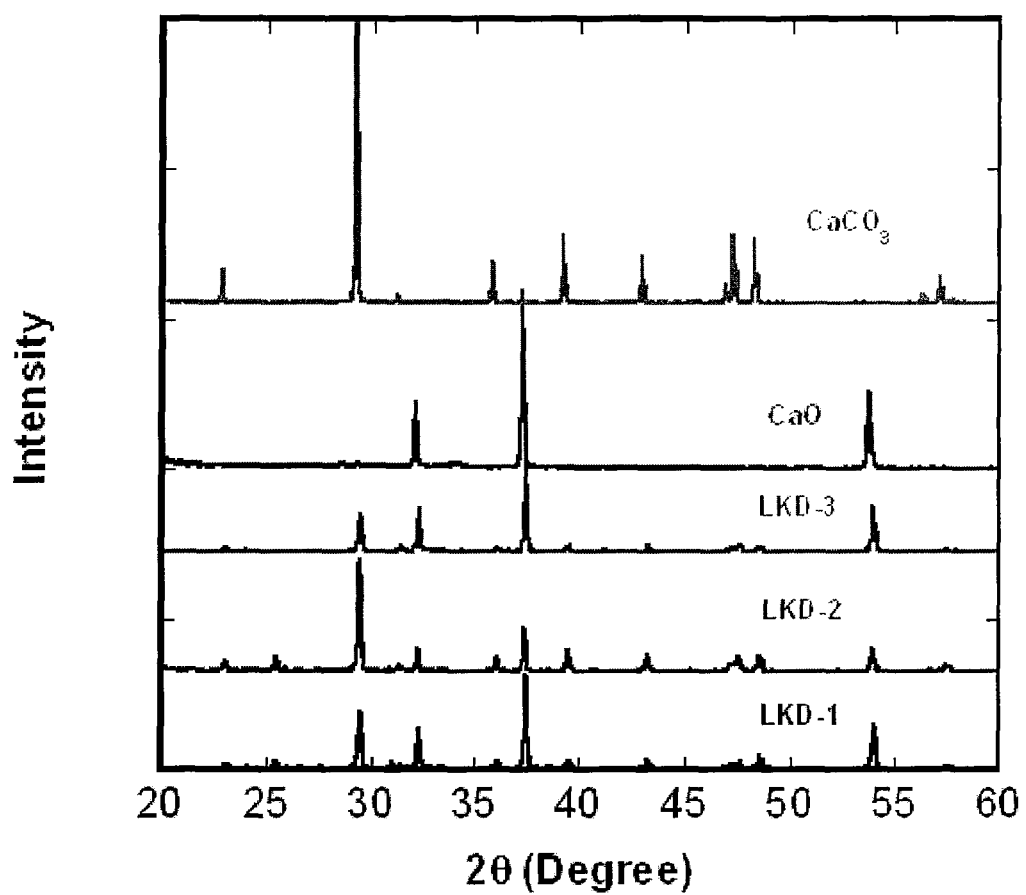
FIG. 8 shows powder XRD plots of various LKD samples from different sources, compared to CaO and $CaCO_3$. The LKD samples provided similar XRD patterns, each showing the characteristic CaO and $CaCO_3$ peaks.
Figure 9:
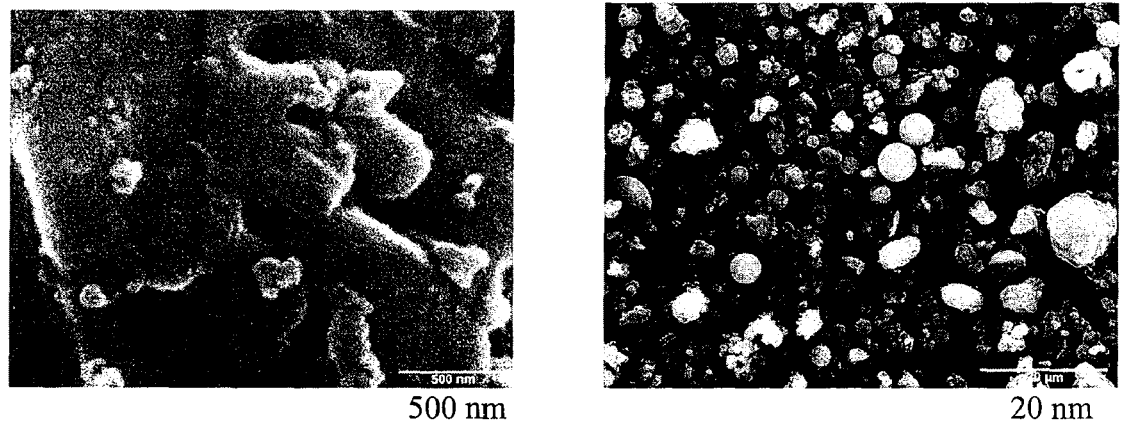
FIG. 9 illustrates scanning electron micrographs (SEM) of one LKD sample (LKD-2) under two different resolutions (bars at lower right equal to 500 nm and 20 nm, respectively).

Powder XRD plots of LKD samples are illustrated in FIG. 8, which compares the powder XRD plots of LKD-1, LKD-2, and LKD-3 to CaO and $CaCO_3$. The LKD samples provided similar XRD patterns, each showing characteristic CaO and $CaCO_3$ peaks, indicating that the major components of LKD are CaO and $CaCO_3$. FIG. 9 illustrates scanning electron micrographs (SEM) of one LKD sample (LKD-2) under two different resolutions.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A recyclable esterification or transesterification catalyst system comprising cement kiln dust, lime kiln dust, or a combination thereof, and a $(C_1-C_5)$alkanol, wherein the surface area of the cement kiln dust or lime kiln dust is about 0.05 $m^2$ per gram to about 10 $m^2$ per gram, and wherein the cement kiln dust or lime kiln dust has been activated by contact with the $(C_1-C_5)$alkanol at a temperature of about 30° C. to about 100° C.

2. The catalyst system of claim 1 wherein the kiln dust comprises one or more of calcium oxide (CaO), calcite ($CaCO_3$), anhydrite ($CaSO_4$), sodium, potassium, magnesium, or quartz ($SiO_2$).

3. The catalyst system of claim 1 wherein the kiln dust contains about 10 mass % to about 65 mass % calcium atoms, and at least 15 wt. % calcium oxide.

4. The catalyst system of claim 1, further comprising a solid acid, a molecular sieve, or both.

5. The catalyst system of claim 4 wherein the acid comprises acidic mesoporous aluminum silicate mixed oxide particles.

6. The catalyst system of claim 1 wherein the $(C_1-C_5)$ alkanol is methanol or ethanol.

7. The catalyst system of claim 1 wherein the surface area of the kiln dust is about 0.1 $m^2$ per gram to about 5 $m^2$ per gram.

8. The catalyst system of claim 1 further comprising a fatty acid or an ester.

9. A method for preparing a fatty acid $(C_1-C_5)$alkyl ester comprising contacting a glyceride-containing vegetable or animal oil with an effective amount of a cement kiln dust, a lime kiln dust, or a combination thereof, and a $(C_1-C_5)$alcohol to provide a reaction mixture, under conditions so that the kiln dust catalyzes formation of a corresponding vegetable oil-derived, or animal oil-derived, fatty acid $(C_1-C_5)$alkyl ester, and glycerol.

10. The method of claim 9 wherein the molar ratio of the $(C_1-C_5)$alcohol to the glyceride-containing vegetable or animal oil is about 600:1 to about 3:1.

11. The method of claim 9 wherein the $(C_1-C_5)$alcohol is methanol or ethanol.

12. The method of claim 9 wherein the kiln dust is recovered and reused in a subsequent method for preparing a fatty acid $(C_1-C_5)$alkyl ester.

13. The method of claim 9 wherein the fatty acid portion of the glyceride-containing vegetable or animal oil comprises an optionally unsaturated $C_{10}-C_{24}$ alkyl chain, and wherein the $C_{10}-C_{24}$ alkyl chain optionally comprises 1, 2, 3, or 4 sites of unsaturation, epoxidation, hydroxylation, or a combination thereof.

14. The method of claim 9 wherein the formation of the ester is carried out without added solvent other than the $(C_1-C_5)$alcohol.

15. The method of claim 9 wherein the formation of the vegetable oil-derived, or animal oil-derived, fatty acid $(C_1-C_5)$alkyl ester is carried out at above about 40° C., and optionally at a pressure greater than 1 atmosphere.

16. The method of claim 9 wherein the kiln dust is present in at least about 0.5 wt. % with respect to the weight of the glyceride-containing vegetable or animal oil.

17. The method of claim 9 wherein the kiln dust and the $(C_1-C_5)$alcohol are contacted prior to contacting the kiln dust and the $(C_1-C_5)$alcohol with the vegetable oil-derived, or animal oil-derived, fatty acid.

18. The method of claim 17 wherein the kiln dust and the $(C_1-C_5)$alcohol are heated prior to contact with the vegetable oil-derived, or animal oil-derived, fatty acid.

19. The method of claim 9 wherein the glyceride-containing animal oil comprises free fatty acids and optionally water, and the method further comprises:
   immobilizing the free fatty acids on a solid acid;
   optionally drying the animal oil by contacting the animal oil with a molecular sieve; and
   optionally separating the molecular sieve and the immobilized free fatty acids from the glyceride-containing animal oil prior to contacting the glyceride-containing animal oil with the kiln dust.

20. The method of claim 9 wherein the fatty acid $(C_1-C_5)$ alkyl ester product comprises about 50 ppm to about 1000 ppm of calcium atoms.

21. A method for preparing fatty acid $(C_1-C_5)$alkyl esters from a feedstock that comprises one or more fatty acids and optionally one or more fatty acid glycerol esters comprising:
   combining the feedstock, the catalyst system of claim 1, an acid, and molecular sieve particles, under conditions wherein the kiln dust catalyzes the formation of fatty acid $(C_1-C_5)$ alkyl esters, and glycerol when a fatty acid glycerol ester is present.

22. A method for preparing fatty acid methyl esters from a feedstock that comprises one or more fatty acids and optionally one or more fatty acid glycerol esters comprising:
   preparing a suspension that comprises cement kiln dust, lime kiln dust, or a combination thereof, methanol, and molecular sieve particles;
   heating the suspension to above about 40° C.;

combining the suspension with the feedstock to provide a reaction mixture;

heating the reaction mixture to provide the fatty acid methyl esters; and separating the fatty acid methyl esters from the reaction mixture.

23. A method for preparing fatty acid methyl esters from a feedstock that comprises poultry fat comprising:

combining poultry fat comprising free fatty acids with a solid acid so as to immobilize free fatty acids on the solid acid;

combining the poultry fat with molecular sieve particles to provide dried poultry fat;

optionally filtering the solid acid and immobilized free fatty acids from the poultry fat, and optionally filtering the molecular sieve particles from the dried poultry fat;

combining the poultry fat with the catalyst system of claim 1, wherein the catalyst system comprises methanol, to provide a reaction mixture;

heating the reaction mixture to above about 40° C. to provide the fatty acid methyl esters; and separating the fatty acid methyl esters from the reaction mixture.

24. The method of claim 23 wherein the suspension of kiln dust and methanol comprises about 0.1 wt. % to about 25 wt. % of kiln dust, with respect to the weight of the dried poultry fat.

25. A method for producing methyl soyate comprising: contacting soybean oil, methanol, and an effective amount of cement kiln dust, lime kiln dust, or a combination thereof, under conditions wherein the kiln dust catalyzes the formation of glycerol and the methyl soyate.

26. A recyclable esterification or transesterification catalyst system comprising kiln dust or Portland cement, and a $(C_1-C_5)$alkanol, wherein the surface area of the kiln dust or Portland cement is about 0.05 m² per gram to about 10 m² per gram, and wherein the kiln dust or Portland cement has been activated by contact with the $(C_1-C_5)$alkanol at a temperature of about 20° C. to about 100° C., further comprising a solid acid, a molecular sieve, or both, wherein the acid comprises acidic mesoporous aluminum silicate mixed oxide particles.

* * * * *

UNITED STATES PATENT AND TRADEMARK OFFICE
CERTIFICATE OF CORRECTION

| | | |
|---|---|---|
| PATENT NO. | : 7,906,665 B2 | Page 1 of 1 |
| APPLICATION NO. | : 12/121918 | |
| DATED | : March 15, 2011 | |
| INVENTOR(S) | : Lin et al. | |

It is certified that error appears in the above-identified patent and that said Letters Patent is hereby corrected as shown below:

On Title page 2, under "Other Publications", in column 2, line 23, delete "$^{1}H^{29}Si$" and insert -- $^{1}H$-$^{29}Si$ --, therefor.

In column 9, line 25, delete "NIH3" and insert -- $NH_3$ --, therefor.

In column 22, line 32, delete "transesterfication" and insert -- transesterification --, therefor.

Signed and Sealed this
Twenty-eighth Day of June, 2011

David J. Kappos
*Director of the United States Patent and Trademark Office*